(12) United States Patent
Leonhardt et al.

(10) Patent No.: US 9,384,549 B2
(45) Date of Patent: Jul. 5, 2016

(54) DEVICE AND METHOD FOR PROCESSING TOMOGRAPHIC DATA

(71) Applicant: Dräger Medical GmbH, Lübeck (DE)

(72) Inventors: Steffen Leonhardt, Aachen (DE); Tim Baier-Löwenstein, Herrnburg (DE); Stefan Mersmann, Lübeck (DE); Robert Pikkemaat, Lübeck (DE); Eckhard Teschner, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 0 days.

(21) Appl. No.: 14/748,638

(22) Filed: Jun. 24, 2015

(65) Prior Publication Data
US 2015/0379706 A1    Dec. 31, 2015

(30) Foreign Application Priority Data

Jun. 25, 2014    (DE) .......................... 10 2014 009 439

(51) Int. Cl.
| G06K 9/00 | (2006.01) |
| G06T 7/00 | (2006.01) |
| A61B 5/053 | (2006.01) |
| A61B 6/03 | (2006.01) |
| A61B 8/13 | (2006.01) |
| G06T 11/00 | (2006.01) |

(52) U.S. Cl.
CPC ............. *G06T 7/0012* (2013.01); *A61B 5/0536* (2013.01); *A61B 6/032* (2013.01); *A61B 8/13* (2013.01); *G06T 11/003* (2013.01); *G06T 2207/10081* (2013.01); *G06T 2207/30048* (2013.01); *G06T 2207/30061* (2013.01); *G06T 2211/40* (2013.01)

(58) Field of Classification Search
None
See application file for complete search history.

(56) References Cited

U.S. PATENT DOCUMENTS

| 3,310,049 | A | 3/1967 | Clynes |
| 4,075,482 | A | 2/1978 | Perilhou |
| 4,149,081 | A | 4/1979 | Seppi |
| 4,486,835 | A | 12/1984 | Bai et al. |
| 4,806,867 | A | 2/1989 | Hanawa et al. |
| 5,052,395 | A | 10/1991 | Burton et al. |
| 5,184,624 | A | 2/1993 | Brown et al. |
| 5,272,624 | A | 12/1993 | Gisser et al. |
| 5,311,878 | A | 5/1994 | Brown et al. |
| 5,807,251 | A | 9/1998 | Wang et al. |
| 6,236,886 | B1 | 5/2001 | Cherepenin et al. |
| 6,647,283 | B2 * | 11/2003 | Klotz ............... A61B 6/481 378/21 |
| 7,561,658 | B2 * | 7/2009 | Hempel ............ A61B 6/032 378/19 |
| 8,374,309 | B2 * | 2/2013 | Donath ............. A61B 6/032 378/145 |
| 2009/0067570 | A1 * | 3/2009 | Mori ................. A61B 6/032 378/8 |

FOREIGN PATENT DOCUMENTS

| DE | 601 24 541 T2 | 9/2007 |
| DE | 10 2012 214 786 A1 | 5/2014 |
| EP | 1 292 224 B2 | 12/2009 |
| WO | 00/18 299 A1 | 4/2000 |

* cited by examiner

*Primary Examiner* — Shefali Goradia
(74) *Attorney, Agent, or Firm* — McGlew and Tuttle, P.C.

(57) ABSTRACT

A device and a method (100) for the processing of data (501), which were obtained by an imaging method, make possible an improvement in a location-specific visualization of the perfusion of the lung. With a reference to a comparison variable, a location-specific variable (503), characteristic of a period of observation, regarding the perfusion of the lung and heart region, is determined and provided as an output signal.

34 Claims, 13 Drawing Sheets

DEVICE AND METHOD FOR PROCESSING TOMOGRAPHIC DATA

CROSS REFERENCE TO RELATED APPLICATIONS

This application claims the benefit of priority under 35 U.S.C. §119 of German Patent Application DE 10 2014 009 439.1 filed Jun. 25, 2014, the entire contents of which are incorporated herein by reference.

FIELD OF THE INVENTION

The present invention pertains to a device and a method for the processing and visualization of data, obtained by means of a medical device suitable for generating data for imaging, on a perfusion and a ventilation of the lung or areas of the lung, as well as on the perfusion of the heart.

BACKGROUND OF THE INVENTION

Devices for electroimpedance tomography (EIT) are known from the state of the art. These devices are designed and provided for generating an image, a plurality of images or a continuous sequence of images from signals obtained by means of electroimpedance measurements and by means of data and data streams obtained therefrom. These images or sequences of images show differences in the conductivity of various body tissues, bones, skin and bodily fluids (blood, lymphatic fluid, cerebrospinal fluid) and organs (lung, heart), which are useful for a diagnosis of diseases, clinical pictures.

U.S. Pat. No. 6,236,886 describes an electroimpedance tomograph containing an array of a plurality of electrodes, feeding of current to at least two electrodes and a method with an algorithm for image reconstruction for determining the distribution of conductivities of a body, such as bones, skin and blood vessels in a basic design with components for detection of signals (electrodes), processing of signals (amplifier, A/D converter), feeding of current (generator, voltage-current converter, current limitation), components for control (mC). The electroimpedance tomograph makes possible a visualization of changes in conductivity within a heart beat and the monitoring of the blood streams in the heart and in the vessels, as well as time dependencies in the perfusion of heart regions in the form of an impedance cardiogram with additional information on the heart function. By means of this visualization, further application possibilities are possible for recognizing internal hemorrhages, external inflammations, examinations on digestive organs, tumor monitoring, inflammations of the breast and various types of diseases of the lung. Moreover, a monitoring of changes in temperature of internal organs is possible.

In U.S. Pat. No. 5,807,251, it is explained that it is known in the clinical application of EIT to provide a set of electrodes, which are arranged at a defined distance from one another, for example, about the thorax of a patient in electrical contact with the skin, and to apply an electric current or voltage input signal each alternatingly between various or all of the possible pairs of electrodes arranged adjacent to one another. While the input signal is applied to one of the pair of electrodes arranged adjacent to one another, the currents or voltages between each pair of the remaining electrodes arranged adjacent to one another are measured and the measurement data obtained are processed in the known manner to obtain a visualization of the distribution of the specific electric resistance over a cross section of the patient, about which the ring of electrodes is arranged, and to display same on a display screen.

It is known from U.S. Pat. No. 5,272,624 to use a medical electroimpedance imaging method using set current patterns, which are fed into the feeding electrodes.

U.S. Pat. No. 5,184,624 shows an array of a plurality of electrodes for an electroimpedance measurement on a body, with feeding of electric current via a pair of electrodes into the body and detection of voltage potentials at the body via the remaining pairs of electrodes. Two electrodes each from the plurality of electrodes, which are arranged in the manner of a circulation about the body one after the other, are thereby selected for the feeding pair of electrodes, and a plurality of the remaining electrodes are used as pairs of electrodes for detecting the voltage potentials.

In U.S. Pat. No. 4,486,835 is described a device for electroimpedance tomography, with which the feeding of electric signals to selected first pairs of electrodes and the detection of electric signals at selected second pairs of electrodes with a preset sequence by means of a multiplexing device is carried out on a body, and is then forwarded to a calculation device coupled to the multiplexing device for the determination of electric properties of a plurality of local regions of the body. These local regions are thereby classified into a three-dimensional imaging grid structure in the body and in an iterative process, the electric conductivity at the plurality of local regions is continuously updated.

U.S. Pat. No. 5,311,878 describes an electroimpedance tomography method and device for real-time imaging. Electroimpedance measured signals from two selected adjacent electrodes are fed to a digital signal processing by electrodes arranged around a thorax with simultaneous feeding of a feeding current in selected electrodes and real-time images are generated by means of computer-based reconstruction.

Besides devices for electroimpedance tomography (EIT), other medical devices that are suitable for imaging, for example, the widest variety of radiological devices, such as X-ray devices, computer tomographs (CT), nuclear magnetic resonance (NMR) devices, nuclear spin or magnetic resonance tomographs (MRT, MRI), as well as also sonographic devices for cardiological, angiological, as well as prenatal or neonatal imaging, which make possible a real-time imaging and a providing of signals or image data, in the area of health care, are being used.

U.S. Pat. No. 3,310,049 A describes a method for determining the heart volume with ultrasound.

An ultrasound-pulse Doppler device for the sonographic determination of the functional capacity of the heart (cardiac output) is known from U.S. Pat. No. 5,052,395 A.

Thus, an X-ray tomography system based on gamma radiation is known from U.S. Pat. No. 4,075,482 A.

U.S. Pat. No. 4,806,867 A shows a magnetic resonance imaging system.

A device for improved image reconstruction of computer tomograms is described in U.S. Pat. No. 4,149,081 A.

A contrast medium, which is introduced into the patient invasively via an access, is usually used in a radiological-cardiological examination by means of such computer tomographs (CT) according to the state of the art. Such a contrast medium, especially when a radioactive isotope is used thereby, represents an extraordinary physical burden for the body and thus makes a continuous imaging monitoring of vital functions of the heart and lung impossible. For generating analyzable images on the condition of the coronary vessels of the heart, it is, moreover, necessary to take the tomographic pictures in the rest phases of the heart or to determine the corresponding useful data by means of reprocessing the tomographic pictures. The tomographic pictures are combined in this case in connection with an electrocardiogram (ECG) by means of two proven methods, the so-called "prospective ECG triggering" or the so-called "ECG gating." In "prospective ECG triggering," the rest phases of the heart are determined by means of ECG and synchronized with the tomographic pictures, in which the patient is then transilluminated layer by layer by table feed. Thus, no real-time total picture of the heart takes place at the same time, but rather the individual pieces of information obtained layer by layer are put together later. In "ECG gating," a tomographic real-time picture of the entire heart and at the same time a continuous detection of ECG signals are taken in a so-called "spiral CT," in which the rotation of the tubes and the table feed take place at the same time. The tomographic pictures are processed by means of the "ECG gating" with inclusion of the ECG signals after the examination and analyzable images are generated therewith. A drawback in both methods is that the computer tomograph (CT) additionally needs an ECG signal as an external signal for synchronization; moreover, it is especially disadvantageous in "ECG gating" that the patient may not breathe during the tomographic examination by means of spiral CT and that the reprocessing of the acquired data is very time-consuming, and thus the result is not available during the examination itself, but rather only delayed in time. Also in the use of magnetic resonance tomographs (MRT), both a synchronization with an electrocardiogram (ECG) for combining data from a plurality of cardiac cycles into complete images and a use of contrast media are usual in order to improve the resolution and the contrast of the tomographic pictures. These exemplary embodiments for imaging by means of MRT or CT in the cardiological environment are applicable to the imaging (angiology/angiography) of the lung by means of MRT, CT in the basic sense.

Moreover, these exemplary embodiments clearly show that devices for electroimpedance tomography (EIT) in comparison to magnetic resonance tomographs (MRT) and also computer tomographs (CT) have marked advantages and essentially regarding the following aspects:

EIT has a real-time functionality
EIT does not require coupling to ECG
EIT does not require contrast medium.

As for sonographic devices for cardiological, angiological, prenatal or neonatal imaging, it should be noted that these devices are limited in use to temporary examinations, since the transducer must be guided in connection with the contact gel by the user and the alignment of the transducer, as well as the function of the contact gel must be continually visually observed by the user during the examination. The following advantages arise from this:

EIT does not require contact gel
EIT does not require continuous monitoring of function by the user.

Thus, electroimpedance tomography (EIT) is, unlike the other medical devices suitable for imaging (X-ray devices, computer tomographs, magnetic resonance tomographs, sonographic devices) cited, suitable for a continuous and long-lasting imaging, especially of the lung as well as the lung and heart, without causing a considerable physical burden or discomfort for the patient.

EP 1 292 224 B2 describes a method and a device for the visualization of data that were obtained by means of electroimpedance tomography. Various special modes for analysis are described, on the basis of which an analysis of the condition of a lung of a patient is provided. Thus, a relative mode is provided, which processes regional changes of a two-dimensional distribution of the ventilation for a past period. Furthermore, a perfusion mode is provided, which processes a two-dimensional distribution of the lung perfusion in a past period of a cardiac cycle. Moreover, a phase shift mode is provided, which processes a dynamics of the ventilation. Additional modes described in this EP 1 292 224 B2 are absolute mode, time constant mode and a regional spirometry mode. The various modes are used for distinguishing various lung conditions. One of the modes or a plurality of these modes is/are selected one after the other for operation for distinguishing various lung conditions. It is common to all modes described in this EP 1 292 224 B2 that no modes and no combination of modes are provided, which makes possible or make possible a shared visualization or processing of perfusion and ventilation.

In the respiration of a patient, especially in intensive care, it is of central importance that the lung of the patient be both ventilated and perfused as best as possible. For, only if an as good as possible perfusion and an as good as possible ventilation over as variable as possible regions of the entire available lung volume is given can the gas exchange, i.e., the introduction of oxygen from the lung into the blood circulation and the transfer of carbon dioxide from the blood circulation via the lung out of the patient take place effectively.

Depending on the constitution, medication and clinical picture of the patient and depending on the settings of the ventilation on a ventilator (also known as a respirator), by means of which the patient is ventilated, the following different physical basic constellations A-D in various local lung regions arise without direct relation to special disease conditions (e.g., atelectasis, emphysema, pneumonia, embolism) in the lung of the patient:

Constellation A: Lung regions with sufficient ventilation and with sufficient perfusion,
Constellation B: Lung regions with sufficient ventilation and with insufficient perfusion,
Constellation C: Lung regions with insufficient ventilation and with sufficient perfusion,
Constellation D: Lung regions with insufficient ventilation and with insufficient perfusion.

This distinction into four constellations in the lung is a common simplified classification in the state of the art, as it is also carried out in EP 1 292 224 B2.

EIT is able, in a spatially resolved manner, to differentiate between perfusion and ventilation from the impedance differences between air/gas and blood. A plurality of heart beat cycles are present in a breath of a patient at the same time. Blood flows into the lung and also out again with each heart beat.

The heart beat cycles have a certain variability in the heart rate and are asynchronous to breathing and different from the respiration rate.

If an EIT sequence of images of local impedance changes or impedances of various regions of the lung for one or more breaths is now observed as a type of overlay consisting of local cardiac- and perfusion-related impedance changes (signals) CPRS (Cardiac and Perfusion Related Signal) and local ventilation-related impedance changes (signals) VRS (Ventilation Related Signal), then the blood flow (perfusion-related impedance changes) from the lung to the heart and from the heart to the lung overlays the breathing (ventilation-related impedance changes).

The cardiac- and perfusion-related impedance changes (CPRS) are thereby divided into cardiac-related impedance changes (signals) CRS (Cardiac Related Signal), which are essentially based on the respective degree of filling of the heart and perfusion-related impedance changes (signals) PRS (Perfusion Related Signal), which are based on the blood distribution (pulmonary perfusion) in the lung tissue.

The result of the overlay between VRS and CPRS, or PRS is that in the sequence of images it is not possible to visually recognize how the constellation regarding perfusion (PRS) and ventilation (VRS) in a local lung region is in each case. In addition, the visual recognizability is made more difficult, on the one hand, by impedance differences of lung regions filled with air compared to the surrounding tissue (muscles, skin, bones) being markedly more variable than the impedance differences of lung regions filled with blood compared to the surrounding tissue (muscles, skin, bones) and thus the CPRS compared to the VRS has a markedly lower signal. In addition, the visual recognizability and quantitative analysis of the perfusion is made more difficult by the phase shifting of the blood flow due to the pulse transit time between heart and lung tissue. The human eye and in connection therewith the cognitive attention naturally follow a movement in the image, in this case the progression of the blood flow in the sequence of images and are thereby at the same time hardly able to determine the strength and its changes of a signal at a defined location over a plurality of images of the sequence of images.

A location-related observation of various lung regions at an observation point in time over time in relation to the beginning of the pulse wave at the heart reveals in a comparison of the perfusion signals of two different regions (region A, region B) of the lung that in the one region (region A) the perfusion is given with a certain quantity, while at the same observation point in time in a different region (region B) the perfusion thereof is quantitatively markedly different. This is explained in that the pulse wave originating from the heart does not reach the various regions of the lung at the same time, but rather takes place delayed differently over time with propagation of the pulse wave into the blood vessels of the lung depending on the vessel length and on the vessel properties (flow resistance, elasticity). This delay becomes apparent as a phase shift between the perfusion signals.

This phase shift is perceived in the EIT sequence of images in a visual analysis, so to speak, as a "progression of the blood flow," which in reality takes place in the lung tissue in this form, but neither in real time nor quantitatively over time in this form. Therefore, adding up the quantities of a plurality of signals without including the phase information at a point in time over a plurality of regions does not produce a quantitative overall image of the perfusion over a plurality of regions of the lung. Partly due to these phase differences in the blood flow between various regions of the lung, an adding up of perfusion signals of a plurality of lung regions thus produces a partial extinction of the perfusion signals with one another, such that no utilizable quantifiable statement on the perfusion of the entire lung or regions of the lung is possible in this way. Also, an adding up over time of a plurality of perfusion signals at a single location or a plurality of defined locations, for example, over a breath or a plurality of breaths, parts of a breath, such as inspiration and expiration or a plurality of breaths is not suitable to generate local images, from which differences in the perfusion between various regions of the lung are clearly and unambiguously obvious. In an adding up over one breath, for example, an adding up over a plurality of heart beat cycles arises, on the one hand, such that for a defined location, the perfusion in one breath fluctuates repeatedly and thereby blood flows in and then flows out again at this defined location, such that the perfusion also cannot, on average, be quantitatively determined for this single location.

SUMMARY OF THE INVENTION

An object of the present invention is to provide a method, a device and a system for processing and visualizing data obtained by means of a medical device suitable for generating data for imaging, for example, of an electroimpedance tomography device, which device provides a quantifiable analysis regarding a perfusion of at least one region of the lung or of at least one region of the lung and of the heart each.

Another object that is closely connected with the first mentioned object arises therefrom to obtain an improvement of the location-related analyzability regarding the perfusion of at least one region of the lung or of at least one region of the lung and the heart each on the basis of provided data of an electroimpedance tomography device or by means of an improved electroimpedance tomography system.

These and other objects are accomplished by the method with the features according to the invention and by a device with device features of the invention. The object is, moreover, accomplished by a system according to the invention.

Moreover, the method may also be provided as a computer program or computer program product, such that the scope of protection of the present application is likewise extended to the computer program product and the computer program.

According to a first aspect of the present invention, in a method according to the present invention for processing and visualizing data obtained by means of a medical device suitable for imaging regarding a perfusion of at least one region of the lung or of at least one region of the lung and of the heart each, data of a medical device suitable for imaging in a sequence of steps are processed, such that a quantifiable analysis regarding a perfusion of at least one region of the lung or of at least one region of each of the lung and of the heart is made possible.

The sequence of steps is divided into the following steps:
Providing a quantity of data based on cardiac- and perfusion-related signals (CPRS) via a signal pattern in the period of observation of at least one location over a period of observation;
Determining and providing phase information on the cardiac- and perfusion-related signals in relation to at least one comparison variable,
Processing the quantity of data Based on CPRS regarding the perfusion of regions of the lung or regions of the lung and of the heart of a patient, taking into account the determined phase information for a determination and providing of a quantity of data of at least one location- and perfusion-related variable characteristic of the period of observation; and
Generating an output signal for a location-related visualization of the quantity of data of the at least one location- and perfusion-related variable characteristic of the period of observation.

This sequence of steps of the processing of data is continuously repeated in a continuous sequence in the method according to the present invention. The processed data are continuously provided as output signals hereby, preferably suitable for an image visualization. In the sense of the present invention, additional steps according to other or preferred embodiments are thereby each included by themselves or combined with each other.

Some of the terminology used within the framework of this patent application is explained below in detail.

In the sense of the present invention period of observation is defined as a section of time in a course over time. The beginning and end of such a period of observation are given by events, which are given by the properties of breathing or respiration, properties of cardiac activity, properties or anomalies of cardiological resuscitation and are usually also reflected in the signals of the quantity of data based on CPRS. Examples of cardiac-related periods of observation are a cardiac cycle, a plurality of cardiac cycles, parts of cardiac cycles, such as systole or diastole, time periods of cardiac cycles, which correspond to defined segments or intervals of the ECG (P wave, QRS complex, T wave, U wave, PQ interval, QT interval, ST segment). Examples of breathing-related periods of observation are a breathing cycle, a plurality of breathing cycles, parts of breathing cycles, such as inspiration, inspiratory pause, expiration, expiratory pause, as well as parts of one or more breathing cycles, e.g., a plurality of inspirations, a plurality of expirations. Further periods of observation, especially in case of mechanical ventilation, may be defined pressure levels, such as plateau pressure or PEEP pressure (Positive End Expiratory Pressure, PEEP) or periods of time, which correspond to defined properties of ventilation forms (e.g., Bi-Level Positive Airway Pressure, BiPAP).

Another possible time period for a period of observation results from the possibility that a specific quantity, a so-called bolus, of a special fluid, for example, a saline solution, is fed invasively to the quantity of blood in the body. This bolus flows with the blood circulation into the heart and brings about a characteristic signal pattern in the imaging of the lung and/or heart. This signal pattern may be used in conjunction with the time of the invasive bolus administration as a basis for determining a period of observation.

The quantity of data based on CPRS is provided as a quantity of data of EIT data from an electroimpedance tomography (EIT) in a preferred embodiment.

EIT data are thereby defined in the sense of the present invention as the following signals or data:
  EIT raw data, i.e., measured signals, such as voltages or currents, detected with an EIT device by means of a set of electrodes or by means of an electrode belt, assigned to electrodes or sets of electrodes or to positions of electrodes or sets of electrodes on the electrode belt.
  EIT image data, i.e., data or signals that were determined with a reconstruction algorithm from the EIT raw data and reproduce local impedances, impedance differences or impedance changes of regions of the lung or regions of the lung and of the heart of a patient.
  Classified EIT data, i.e., EIT image data or signals that are presorted or preclassified according to preset criteria. The classification may thereby be implemented, for example, by means of a standardized distribution into EIT data or signals that reproduce CPRS impedances, impedance differences or impedance changes and into EIT data or signals that reproduce ventilation-related impedances, impedance differences or impedance changes or ventilation related signals (VRS).
  Specially classified EIT data, i.e., EIT image data or signals that are presorted or preclassified according to special preset criteria. The special classification may thereby be implemented, for example, additionally by means of a standardized distribution into EIT data of signals that comprise essentially perfusion related signals (PRS), impedances, impedance differences or impedance changes of the lung and into EIT data or signals that reproduce cardiac related signals (CRS), impedances, impedance differences or impedance changes of the heart.

In further preferred embodiments, provisions are made in the sense of the present invention for the quantity of data based on CPRS to also be represented as:
  Data of a medical device, which provides an imaging based on computer tomography (CT),
  data of a medical device, which provides an imaging based on X-ray,
  data of a medical device, which provides an imaging based on magnetic resonance tomography (MRT) or nuclear spin tomography
  data of a medical device, which provides an imaging based on sonography (ultrasound).

The phase information of the cardiac- and perfusion-related signals in relation to the at least one comparison variable is preferably determined and provided here by means of mathematical methods for signal and data processing that are based on a phase analysis in the frequency range, an analysis of time delays in the time period or on a cross correlation of the signals in the time period. In the sense of the present invention, phase information includes any kinds of information pertaining to a phase position, a phase difference or phase differences, as well as time delays or time shifts or signals or signal portions in the signal pattern within the period of observation regarding a perfusion of a region or a plurality of regions of the lung or heart on a reference variable or on a comparison variable, for example, on a different region of the lung or heart. Moreover, any kind of a time delay or time shift of signals or signal portions in the signal pattern within the period of observation regarding a ventilation of a region or a plurality of regions of the lung on a reference variable or on a comparison variable, for example, on a different region of the lung is included under the term of a time delay in the sense of the present invention. Time delays of perfusion signals or ventilation signals are to be determined in the time period by means of an analysis of the signal patterns within the period of observation regarding the distance over time between characteristic signal structures, for example, zero crossings, amplitude maxima or amplitude minima, under- or overshooting of threshold values, in the signal pattern or at least of two signals to one another or of a signal to a comparison variable by means of comparison of the signal patterns. Moreover, phase information is characterized in the sense of the present invention as phase shifts present in the spectral range of the cardiac- or perfusion- and/or ventilation-related signals, phase differences or phase positions of various regions, locations, pixels of a region or a plurality of regions of the lung or heart. Likewise, such phase information, which can be determined by means of transformations, for example, FFT, Laplace transformation, Z transformation, Wavelet transformation, of the quantities of data of cardiac- and perfusion-and/or ventilation-related signals are included in the sense of the present invention and can be determined as phase information by means of corresponding retransformation.

In a preferred embodiment, a signal or signal pattern in the period of observation of another location, different from the at least one location, from the quantity of data based on CPRS is used as a comparison variable.

In another preferred embodiment, a signal or a signal pattern in the period of observation from the quantity of data based on CPRS is used as a comparison variable that characterizes the phase position of the heart. Partly due to the constant change from contraction (systole) of the heart and relaxation (diastole) in the rhythm of the heart beat, the location of the heart is demarcated from the quantity of data based on CPRS as a location-related subquantity of data of impedance changes appearing very similar in the rhythm of the heart beat and is thus suitable as a basis for deriving the comparison variable. Since the propagation of the blood into the heart chamber takes place without considerable delays, the phase positions of the locations which together represent the location of the heart (cardiac region) are only slightly different from one another. This results in time delays of the perfusion within the region of the heart of approx. 20 msec, which leads to phase differences of only approx. 7° to 10° at a heart rate of 60-80 beats per minute. On the basis of these physiological-cardiological connections, it is advantageous to determine the phase position of the heart from the quantity of data based on CPRS and to use this phase position of the heart as a comparison variable for processing the quantity of data based on CPRS regarding perfusion into a location- and perfusion-related variable characteristic of the period of observation.

In another preferred embodiment, a signal or a signal pattern from the quantity of data based on CPRS, which has a lowest indicator on agreement regarding the phase position with the plurality of signals of the quantity of data based on CPRS, is used as a comparison variable in the period of observation. Thus, a kind of "mathematical zero phase," to which the remaining location-related signals of the quantity of data can be mathematically standardized or referred in the further data processing, is advantageously obtained for the quantity of data. The processing of the quantity of data based on CPRS regarding the perfusion of regions of the lung or regions of the lung and of the heart of a patient, taking into account the phase information determined, is used for determining and providing a quantity of data with at least one location- and perfusion-related variable characteristic of the period of observation. The characteristic variable represents an indicator of the perfusion at a defined location or at a plurality of locations of the lung or heart, which is characteristic of the perfusion in the period of observation.

In the sense of the present invention, characteristic location- and perfusion-related variables are defined as any determined variables, which, by means of a mathematical connection, represent an adaptation, matching, evaluation, or weighting of signals or data, sets of signals or data of the at least one location for at least one comparison variable regarding the perfusion. These include, for example, manipulations of signals or signal patterns of the at least one location over a period of observation, such as summations, integrations, formation of mean values, median values and the widest variety of averagings, such as arithmetic mean value, geometric, harmonic or root mean square (RMS) value, maximum and minimum values, relations to maximum values, to minimum values, to mean values or to defined threshold values or defined levels or tolerance ranges.

In a preferred embodiment, the at least one characteristic location- and perfusion-related variable determined on the basis of the phase information is a location-, CPRS, which is synchronized (a synchronized cardiac and perfusion related signals (sCPRS)) with the at least one comparison variable, due to an equalization of the phase difference of the at least one signal from the quantity of data based on CPRS with the at least one comparison variable. Thereby, the CPRS are preferably synchronized in relation to the at least one comparison variable by means of mathematical methods on signal and data processing, which are based on a phase adaptation in the frequency spectrum or on a shift of individual data sets in the time period.

The phase adaptation in the frequency spectrum takes into account the associated location—related phase values, after transformation of the time signals in the frequency range—either frequencies or ranges of frequencies of the signals, which are essentially to be assigned to the cardiac activity. The shifting of individual data sets in the time period shifts the signals or signal patterns in the period of observation in relation to a comparison variable, preferably in relation to a different location than the comparison variable.

In a particularly preferred embodiment, a synchronization for a plurality of signals from the quantity of data based on CPRS is performed via a signal pattern or over a period of observation as a characteristic location- and perfusion-related variable. Thereby, the location-related phase differences are matched to one another by the phases of the signals being synchronized to the phase position of the heart. Thereby, the plurality of signals from the quantity of data based on CPRS reflects an essential part of the lung and also of the heart, such that a quantity of data on location- and perfusion-related characteristic variables regarding the location-related perfusion of the lung and heart is obtained in this way over essential parts of the lung and heart as a quantity of data on synchronized cardiac- and perfusion-related signals (sCPRS) in relation to the phase position of the heart.

In another especially preferred embodiment, a providing of a quantity of data on ventilation-related signals (VRS) takes place in a further step via a signal pattern in the period of observation of at least one location regarding the ventilation of regions of the lung over a period of observation.

In a variant of this further particularly preferred embodiment, a shared providing of a quantity of data, which contains the quantity of data based on CPRS and the quantity of data based on VRS, takes place in the further step.

In a step following this step of shared providing, a distinguishing of the quantity of data based on CPRS from the quantity of data based on VRS takes place in another especially preferred embodiment of the shared providing of data in a further step.

The distinguishing between the CPRS and the VRS takes place by means of mathematical methods and model functions for data separation. As examples of such methods for signal and data analysis and separation, principal component analysis (PCA) and independent component analysis (ICA) may be mentioned here. Principal component analysis (PCA) is based on methods of least squares minimization and the analysis of the highest data variance, and independent component analysis (ICA) is based on model functions based on maximum statistical independencies between the signals to be separated.

The distinguishing of the quantities of data (CPRS, VRS) may thereby also take place by means of mathematical frequency-selective methods (DFT, FFT). Partly due to the difference of the cardiac cycle (heart rate: approx. 60 to 150 bpm) from the breathing cycle (respiration rate: approx. 12 to 45 breaths per minute), a marked difference in the frequency ranges is given and thus a distinguishing in the frequency range between the signal portions associated with perfusion and the signal portions associated with ventilation is sufficiently readily possible.

In another especially preferred embodiment, a quantity of data on synchronized ventilation-related signals (sVRS) is determined and provided in a further step from the quantity of data based on VRS. In the quantity of data on synchronized ventilation-related signals (sVRS), the phase positions of the ventilation-related signals of individual locations to one another are matched to one another or synchronized with each other over time in the period of observation, taking into account the phase information determined. The sVRS offer the advantage that alternating intensities of the ventilation of individual lung regions over the period of observation are matched in the period of observation, for example, for the duration of inspiration or expiration. This is advantageous for further processings of the data, preferably for a reference of the ventilation with the perfusion data. These sVRS therefore form the basis for a matching of the ventilation-related signals with the cardiac- and perfusion-related signals in a further particular embodiment, in which a synchronized ventilation-related quantity of data, synchronized with the perfusion, is determined and provided. In this further particular embodiment, the sVRS are matched in the time reference to the sCPRS and to a synchronized ventilation-related quantity of data (sVRS'), matched to the perfusion.

In another especially preferred embodiment, special regions of interest (ROI) in at least one region of the lung or of the heart are determined in a further step on the basis of the phase information determined. From the phase information, it is possible to combine or group regions or locations of the lung or of the heart with identical or similar phase position into a particular region of interest (ROI). In such a combination of particular regions of interest, locations with identical phase position or similar phase position are combined into perfusion-related regions of interest. The cardiac region in general, as well as the heart chamber may be mentioned as an example of a particular region of interest.

Since the blood propagation and blood distribution in the heart takes place without essential delays, the phase positions of the locations, which together represent the location of the heart, are only slightly different from one another and together form a particular cardiac-related region of interest (Cardiac-Related Region of Interest; CR-ROI). Further examples of cardiac-related regions of interest (CR-ROI) are the pulmonary vein, pulmonary artery, aorta, and lesser or greater pulmonary circulation.

Similarly, there are regions in the lung, in which the blood propagation and blood distribution are similar. Upper, central or downside regions of the left or right lung each or regions of the lung as they can arise or can be derived therefrom, for example, according to the so-called "three-compartment model of the lung" can be mentioned as examples of lung-related regions of interest (Perfusion-Related Region of Interest; PR-ROI).

In a particular embodiment of this further preferred embodiment, the quantity of data based on sCPRS or the quantity of data of the shared providing based on CPRS and VRS is distinguished in a further step on the basis of the phase information and/or the defined regions of interest (ROI, PR-ROI, CR-ROI) into a quantity of data on perfusion-related signals (PRS) of the lung and into a quantity of data on cardiac-related signals (CRS) of the heart and be provided as quantities of data on perfusion-related signals (PRS) of the lung and cardiac-related signals (CRS) of the heart.

In another preferred embodiment, a determination and providing of a variable corresponding to the pumping capacity of the heart takes place in a further step from the quantity of data based on CPRS or sCPRS and/or the defined particular regions of interest (ROI) and/or the quantity of data on synchronized perfusion-related signals (sPRS) of the lung and/or the quantity of data on synchronized cardiac-related signals (sCRS) of the heart. Variables corresponding to the pumping capacity of the heart are, for example, cardiac output, ejection fraction of the heart, or stroke volume of the heart. The term "cardiac output" is often also used for this variable.

In another preferred embodiment, a combination from one of the quantities of data on ventilation-related signals (VRS, sVRS, sVRS') with one of the quantities of data on synchronized perfusion-related signals (sCPRS, sPRS) into a quantity of data of related parameters, which characterize the condition of the lung regarding perfusion and ventilation locally as characteristic location- and perfusion-related variables over the period of observation, takes place in a further step. For this, a ratio from ventilation-related signals and perfusion-related signals is formed. The formation of the ventilation to perfusion ratio (VQ ratio), of the so-called V-to-Q ratio (sV/Q), from VRS or synchronized ventilation-related signals (sVRS, sVRS') to synchronized perfusion-related signals (sPRS), which characterizes the condition of the lung regarding perfusion and ventilation in a location-related manner, is particularly preferred. Thereby, preferably one of the breathing-related periods of observation is selected as a reference of the signals over time, since thereby a qualitative and quantitative statement on perfusion and ventilation for individual regions of the lung related to the physiological connections of the gas exchange in the lung and to breathing or respiration is made possible without time delays from blood exchange, blood flow, blood inflow and outflow into the lung being able to make the statement unfamiliar. The so-called V-to-Q ratio (sV/Q) indicates for individual regions of the lung, whether a region is better perfused than ventilated, is better ventilated than perfused, is perfused and ventilated in a balanced manner or is neither sufficiently ventilated nor perfused. As explained before concerning EP 1 292 224 B2, a division into these four constellations is obtained in an exemplary and advantageous manner here, so that a classification of the V-to-Q ratio (sV/Q) to these four constellations reflects the condition of the lung in a simple and advantageous manner. If the synchronized ventilation-related signals (sVRS, sVRS') are used as ventilation-related signals for forming the ratio, then flow-related delays or delays caused by effects of the positioning of the patient are additionally advantageously reduced in the gas exchange in the lung, and the statement of the ratio (sV/Q) is improved.

Such a statement is very readily suitable for the user to check the settings of the ventilator, such as inspiration pressure, minute volume (MV), expiration pressure, positive-end-expiratory pressure (PEEP).

In another preferred embodiment, a global ventilation-perfusion characteristic value ($sV/Q_{Global}$), which makes possible a statement, which has been reduced to a numerical value, about the average condition regarding ventilation and perfusion of the entire lung, is formed in a further step from the quantity of data on location-related parameters (sV/Q), which characterizes the condition of the lung regarding perfusion and ventilation in a location-related manner, as a characteristic location-related and perfusion-related variable over the period of observation.

In a simplest embodiment the global ventilation-perfusion characteristic value ($sV/Q_{Global}$) is formed as a mean value or as a weighted mean value, but it is also possible to use methods of differential or integral calculus thereby in order to take into account, for example, anomalies of the shape of the lung, such as three-dimensionality or even anomalies of the basic data (EIT, CT, MRT, ultrasound) on which the formation of the quantity of data on location-related parameters (sV/Q) is based.

In a particular embodiment the method makes possible, in a continuous process, a generation of EIT data at the thorax of a patient, a processing and visualization of the EIT data regarding a perfusion of at least one region of the lung or of at least one region of each of the lung and of the heart on at least one location- and perfusion-related variable which is characteristic of the period of observation and a display of the characteristic variable. In this particular embodiment this method makes possible in a sequence of steps a detection of EIT data by means of an electroimpedance tomography device (EIT) by means of an electrode array consisting of a plurality of electrodes arranged at or around the thorax of a patient, a processing and a visualization of the EIT data regarding a perfusion of at least one region of the lung or of at least one region of each of the lung and of the heart a signal pattern of at least one location lying within a period of observation.

In this method for the processing and visualizing of data obtained by means of an electroimpedance tomography device (EIT) regarding a perfusion of at least one region of the lung or of at least one region of each of the lung and of the heart, a signal pattern of at least one location lying within a period of observation by means of an electrode array consisting of a plurality of electrodes arranged at or about the thorax of a patient, the sequence of steps is thereby divided into the following steps:

Feeding an alternating current or an alternating voltage to at least two of the electrodes of the electrode array and detecting measured signals at at least two of the electrodes of the electrode array, whereby in a continuous sequence one after the other another two electrodes from the plurality of electrodes are selected for feeding the alternating current or alternating voltage, and the measured signals are detected with at least two electrodes from the plurality of electrodes, generating and providing a quantity of data based on CPRS by means of a reconstruction algorithm from the measured signals, determining and providing phase information from the perfusion-related signals (CPRS) in relation to at least one comparison variable, processing the quantity of data (CPRS) on signals regarding the perfusion of regions of the lung or regions of the lung and of the heart of a patient, taking into account the phase information determined for a determination and providing of a quantity of data on at least one location- and perfusion-related variable characteristic of the period of observation, generating and providing an output signal to a display device for a visualization of the quantity of data on the at least one location- and perfusion-related variable characteristic of the period of observation, visualizing the quantity of data on the at least one location- and perfusion-related variable characteristic of the period of observation on the display device, whereby the at least one location-related and perfusion-related variable is visualized numerically, graphically or pictorially over the period of observation.

The embodiments described each represent by themselves as well as in combination with each other particular embodiments of the method according to the present invention for the processing and visualizing of data obtained by means of a medical device suitable for generating data for imaging regarding a perfusion of at least one region of the lung or at least one region of each of the lung and of the heart. Advantages resulting from combination or combinations of a plurality of embodiments and further embodiments are thereby nevertheless covered by the idea of the present invention, even if not all combination possibilities of embodiments are each explained in detail for this. The above-described embodiments of the method according to the present invention may also be designed in the form of a computer-implemented method as a computer program product with a computer, whereby the computer is prompted to execute the above-described method according to the present invention, when the computer program is executed on the computer or on a processor of the computer or a so-called "embedded system" as part of a medical device. The computer program may thereby also be stored on a machine-readable storage medium. In an alternative embodiment, a storage medium, which is intended for the storage of the above-described, computer-implemented method and is readable by a computer, may be provided. It lies within the framework of the present invention that not all steps of the method have to be necessarily executed on one and the same computer, but rather they may also be executed on different computers. Also, the sequence of the method steps may possibly be varied. Moreover, it is possible that individual sections of the above-described method may be executed in a separate unit, which can be sold, for example, by itself (e.g., on a data analysis system preferably arranged in the vicinity of the patient) and other parts may be executed on a different unit which can be sold (e.g., on a display and visualization unit, which is arranged, for example, as a part of a hospital information system preferably in a room set up for the monitoring of a plurality of patient rooms), so to say as a distributed system.

The means for accomplishing the object was described above in relation to the method claimed as a first aspect of the present invention. Features, advantages or alternative embodiments mentioned here are also applicable to the other claimed subjects and vice versa. The corresponding functional features of the method are thereby embodied by corresponding subjective modules of a device, in particular by hardware components ($\mu$C, DSP, MP, FPGA, ASIC, GAL), which, for example, can be implemented in the form of a processor, a plurality of processors ($\mu$C, $\mu$P, DSP) or in the form of instructions in a memory, which are processed by the processor.

This results in another aspect of the present invention, which accomplishes the set objects according to the present invention by a device for executing the method for processing and visualizing data obtained by means of a medical device which is suitable for generating data for imaging regarding a perfusion of at least one region of the lung or of at least one region of each of the lung and of the heart. This device suitable for executing the method is designed in such a way as to execute the processing and visualizing of data according to the steps described in the method, as well as also to execute the further steps described in the embodiments each by itself or in combination. Thus, for example, the providing of the quantity of data on perfusion-related signals (CPRS) can take place by means of a data input unit and the generating and providing of the output signal can take place by means of a data output unit. The processing of the data may take place, for example, by means of a calculation and control unit.

The data input unit thereby preferably has such interface elements as, for example, amplifiers, A/D converters, components for surge protection (ESD protection), logic elements and other electronic components for wired or wireless receipt of data and signals, as well as adaptation elements, such as code- or protocol-conversion elements for adapting the signals and data for further processing in the calculation and control unit. The calculation and control unit has elements for data processing, calculation and process control, such as microcontrollers ($\mu$C), microprocessors ($\mu$P), signal processors (DSP), logic components (FPGA, PLD), memory components (ROM, RAM, SD-RAM) and combination variants thereof, for example, in the form of an "embedded system", which are designed as shared with one another and adapted to one another and designed by programming to execute the method for processing and visualizing data obtained by means of a medical device suitable for generating data for imaging regarding a perfusion of at least one region of the lung or at least one region of each of the lung and of the heart. The data output unit is designed for generating and providing the output signal. The output signal is preferably embodied as a video signal (e.g., Video Out, Component Video, S-Video, HDMI, VGA, DVI, RGB) in order to make possible a graphic, numerical or pictorial visualization of the at least one location- and perfusion-related variable, characteristic of the period of observation, on a display unit connected with the output unit either in a wireless or wired manner (WLAN, Bluetooth, WiFi) or on the output unit itself. All the advantages that can be achieved with the method described can be achieved in an identical or similar manner with the described device for executing the method for processing and visualizing data obtained by means of a medical device suitable for generating data for imaging regarding a perfusion of at least one region of the lung or of at least one region of each of the lung and of the heart.

This further aspect of the present invention is continued as a special aspect and additional means for accomplishing the set objects are explained in detail below as an additional device according to the present invention and as a system according to the present invention.

The advantages described for the method according to the present invention can be achieved in an identical or similar manner with the device according to the present invention or with the system according to the present invention, as well as the described embodiments of the device or of the system. Moreover, the described embodiments and their features and advantages of the method are applicable to the device and the system, and the described embodiments of the device and of the system are also applicable to the method.

The device according to the present invention has:
a data input unit
a calculation and control unit and
a data output unit
for a processing and visualizing of data obtained by means of an electroimpedance tomography device (EIT) regarding a perfusion of at least one region of the lung or of the heart, whereby the device is designed to provide by means of the data input unit for a receipt of data and a quantity of data based on CPRS over a course over time of at least one location over a period of observation, whereby the device is designed by means of the calculation and control unit for a determination and providing of phase information of the cardiac- and perfusion-related signals in relation to at least one comparison signal, whereby the device is designed by means of the calculation and control unit for a processing of the quantity of data on signals regarding the perfusion of regions of the lung or regions of the lung and of the heart (CPRS) of a patient, taking into account the phase information determined, for a determination and providing of a quantity of data on at least one location- and perfusion-related variable characteristic of the period of observation, whereby the device is designed by means of the data output unit for generating an output signal for a location-related visualization of the quantity of data on the at least one location- and perfusion-related variable characteristic of the period of observation.

In a further aspect of the present invention, a system for a processing and visualizing of data obtained by means of an electroimpedance tomography (EIT) device regarding a perfusion of at least one region of the lung or of at least one region of each of the lung and of the heart represents a means for accomplishing the objects.

The system according to the present invention is designed as an EIT system and has an electroimpedance tomography device, an arrangement for the processing of electroimpedance tomography data with a data input unit and a display device. The electroimpedance tomography device has an electrode array with a plurality of electrodes, an operating electronic unit, a measured value acquisition and analysis unit and a data processing and calculation unit. The electrode array is arranged on or around the thorax of a patient. At least two of the electrodes of the electrode array are designed for feeding an alternating current or alternating voltage, at least two of the electrodes of the electrode array are designed for detecting measured signals. The operating electronic unit is designed for feeding the alternating current or alternating voltage into the electrodes. The measured value acquisition and analysis unit is designed for detecting the measured signals at the electrodes. The operating electronic unit and the measured value acquisition and analysis unit are designed to carry out the feeding of the alternating current or of the alternating voltage at at least two of the electrodes and the detection of measured signals at at least two electrodes of the electrode array, such that in a continuous sequence one after the other another two electrodes from the electrode array are selected for feeding the alternating current or alternating voltage and the measured signals are detected with at least two electrodes of the electrode array. The data processing and calculation unit is designed to generate a quantity of data on perfusion-related signals (CPRS) via a signal pattern of at least one location lying within a period of observation by means of a reconstruction algorithm from the measured signals and to provide same to the data input unit.

The arrangement for processing and providing electroimpedance tomography data has a calculation and a control unit and a data output unit. The calculation and control unit is designed for determining and providing phase information of the perfusion-related signals in relation to at least one comparison signal.

The calculation and control unit is designed for processing the quantity of data on signals regarding the perfusion of regions of the lung or regions of the lung and of the heart of a patient (CPRS), taking into account the phase information determined, for determining and providing a quantity of data of at least one location- and perfusion-related variable which is characteristic of the period of observation.

The data output unit is designed for generating and providing an output signal for a location-related visualization of the quantity of data on the at least one location- and perfusion-related variable which is characteristic of the period of observation.

The display device is designed to reproduce, on the basis of the output signal, a numerical, graphic or pictorial visualization of the at least one location- and perfusion-related variable characteristic of the period of observation.

In a particular embodiment, the device or the EIT system is designed by means of the calculation and control unit for a synchronization. The calculation and control unit generates, on the basis of the phase information, a quantity of data on synchronized cardiac- and perfusion-related signals (Synchronized Cardiac and Perfusion Related Signals; sCPRS) as a characteristic location- and perfusion-related variable and provides this quantity of data to the data output unit or display device. The generation of the synchronized cardiac- and perfusion-related signal (sCPRS) takes place by means of an equalizing of the phase differences in relation to at least one comparison variable. The at least one comparison variable may be represented, for example, by signals of another location from the quantity of data based on CPRS that is different from the at least one location. The at least one comparison variable may, furthermore, be represented by a phase position of the heart from the quantity of data based on CPRS.

In a special variant, it is also possible for the comparison variable to be represented by signals of at least one location of the greatest phase difference from the quantity of data based on CPRS in comparison to the phase positions of the entire quantity of the locations of the quantity of data based on CPRS.

The calculation and control unit carries out the synchronization by means of a phase adaptation in the frequency spectrum or on the basis of a shifting of the individual data sets in the time period.

In another preferred embodiment of the device or of the EIT system, the calculation and control unit equalizes the phase differences to the phase position of the heart and generates a quantity of data on sCPRS synchronized to the phase position of the heart and provides these to the data output unit or to the display device.

In another preferred embodiment, the device or EIT system is designed with the data input unit to receive a shared quantity of data, which jointly contains CPRS and VRS.

In another preferred embodiment of the device or of the EIT system, the calculation and control unit is designed to distinguish CPRS from ventilation-related signals and to generate from the shared quantity of data a quantity of data based on CPRS and a quantity of data based on VRS and to provide same for the calculation and control unit. For distinguishing between the CPRS and the VRS, the calculation and control unit uses mathematical methods for signal and data analysis and mathematical model functions for data separation, for example, principal component analysis (PCA) or independent component analysis (ICA).

In another preferred embodiment of the device or of the EIT system, the calculation and control unit is designed to match or synchronize the VRS of various regions of the lung with each other in the time reference or in the phase position over a period of observation and to provide same as a quantity of data on sVRS for the data output unit or the display device.

In another preferred embodiment of the device or of the EIT system, the calculation and control unit is designed to match the VRS or the sVRS to the sCPRS in the time reference or in the phase position or to synchronize with same and to provide same as a quantity of data on synchronized ventilation-related signals (sVRS'), synchronized with the perfusion, for the data output unit or the display device.

In another preferred embodiment of the device or of the EIT system, signals of identical or similar phase position are determined by the calculation and control unit based on the phase information determined and combined or grouped into special regions of interest (Regions Of Interest; ROI) regarding the perfusion of the heart (Cardiac-Related Region of Interest; CR-ROI) and regarding the perfusion of the lung (Perfusion-Related Region of Interest; PR-ROI) for at least one region of the lung or of the heart and provided for the data output unit or the display device.

In another preferred embodiment of the device or of the EIT system, the calculation and control unit is designed to distinguish the quantity of data based on sCPRS or the quantity of data of the shared providing of CPRS and VRS based on the phase information and/or on the defined regions of interest (ROI, PR-ROI, CR-ROI) into a quantity of data based on perfusion-related signals (PRS) of the lung and into a quantity of data based on cardiac-related signals (CRS) of the heart and to provide same to the data output unit or the display device as quantities of data on synchronized perfusion-related signals (sPRS) of the lung and synchronized cardiac-related signals (sCRS) of the heart.

In another preferred embodiment of the device or of the EIT system, a variable corresponding to the pumping capacity of the heart is determined by the calculation and control unit from the CPRS or sCPRS and/or the defined special regions of interest (ROI) and/or the synchronized perfusion-related signals (sPRS) of the lung and/or the synchronized perfusion-related signals (sCRS) of the heart and is provided for the data output unit or the display device.

In another preferred embodiment of the device or of the EIT system, the calculation and control unit is designed to combine at least one of the quantities of data on ventilation-related signals (VRS, sVRS, sVRS') with at least one of the quantities of data on synchronized perfusion-related signals (sCPRS, sPRS) into a quantity of data on location-related parameters regarding perfusion and ventilation and to provide same for the data output unit or the display device. For this purpose, a ratio, the so-called V-to-Q ratio (sV/Q), of VRS or synchronized perfusion-related signals (sVRS, sVRS') to the synchronized perfusion-related signals (sPRS) of the lung, is formed and provided as a quantity of data regarding the location-related condition of the lung regarding perfusion and ventilation for the data output unit or the display device.

In a special variant of this further preferred embodiment of the device or of the EIT system, a global ventilation-perfusion characteristic value ($sV/Q_{Global}$) is formed by the calculation and control unit from the quantity of data on location-related parameters ($sV/Q$), which characterizes the condition of the lung regarding perfusion and ventilation in a location-related manner, as a characteristic location-related and perfusion-related variable over the period of observation and is provided for the data output unit or the display device. This global ventilation-perfusion characteristic value ($sV/Q_{global}$) delivers a statement, which is reduced to a numerical value, on a condition regarding ventilation and perfusion of the entire lung.

The global characteristic value $sV/Q_{global}$ Global determined from the quantity of data on location-related parameters ($sV/Q$) may thereby be determined both as a mean value $sV/Q_{Mean}$, $sV/Q_{Median}$, as a minimum value $sV/Q_{Min}$ or as a maximum value $sV/Q_{Max}$ and be provided for the data output unit or the display device.

In another preferred embodiment, the data output unit or the display device is designed to output the quantity of data on location-related parameters ($sV/Q$) as a numerical, graphic or pictorial visualization, standardized to one of the global ventilation-perfusion characteristic values $sV/Q_{Mean}$, $sV/Q_{Median}$, $sV/Q_{Min}$, $sV/Q_{Max}$.

The present invention is now explained in detail by means of the following figures and the associated figure descriptions without limitations of the general ideas of the present invention. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
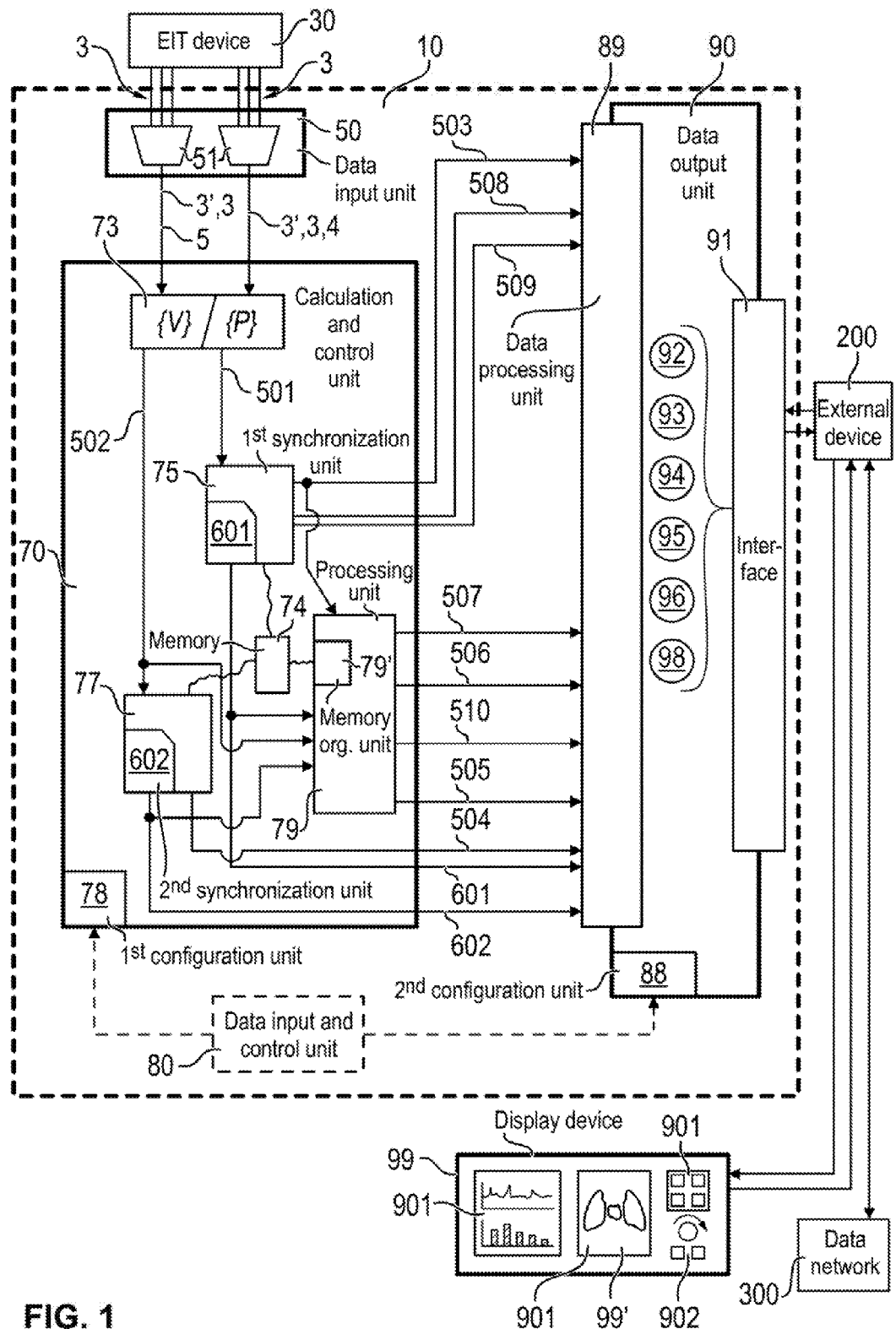
FIG. 1 is a schematic view of functional elements for a processing of EIT data.

FIG. 1 schematically shows an arrangement 10 of functional elements for a processing of EIT data 3. This arrangement 10 comprises a data input unit 50, a calculation and control unit 70 and a data output unit 90 as basic components. Moreover, a display device 99 connected with the data output unit 90 is shown in this FIG. 1. The display device 99 comprises a visualization means 901, such as display elements, display screens, displays for visualization of graphs, curve courses, diagrams or images or even numerical value displays for the reproduction of numerical values. Moreover, the display device 99 comprises input and control elements 902, such as switches, buttons, knobs, and rotary knobs. A contact-sensitive display (touchscreen) with combination of input and visualization functionalities represents a special embodiment variant. The data input unit 50 reads in data from an EIT device 30 as EIT data 3 at least one data input 51 or a plurality of data inputs 51. The EIT device 30 in this FIG. 1 is connected to the arrangement 10 as an external device. However, in the sense of the present invention, it is also included that, on the one hand, the EIT device 30 may be designed as a component of the arrangement 10, and, on the other hand, also that the arrangement 10 may be designed as a part of the EIT device 30. After the reading in, the data input unit 50 holds the data for further processing either in an unchanged format as EIT data 3 or in a form adapted for further processing as EIT data 3'. In a special variant, the EIT data 3, 3' may already be available separately at the data inputs 51, for example, as EIT perfusion data 4 and as EIT ventilation data 5. The data output unit 90 is designed to provide both data at an interface 91 for a visualization as numbers 92, images 93, diagrams 94 or curves, curve courses, signal patterns over time 95, as well as data sets, especially in the form of data compilations 96, 98 on a display device 99 (display screen, monitor, visual display unit). In the sense of the present invention, providing is defined as any form of providing signals or data for forwarding, output, visualization, display, printout, sending, or for further processing to other devices or to parts of devices. In this FIG. 1, the display device 99 is connected to the data output unit 90 as an external device via the interface 91. However, in the sense of the present invention, it is also included that the display device 99 may be designed as an internal unit of the data output unit 90 or even of the arrangement 10. By means of the interface 91, for example, a wireless or wired providing of data in a data network 300 (LAN, WLAN, Ethernet), the wireless or wired providing of data for mutual transmission of measured values and control data (e.g., USB, RS232, RS485, FireWire, NMEA 0183, IrDA, Bluetooth, CAN, UMTS (SMS, MMS)) in the data exchange with various other external devices 200 (anesthesia devices or ventilators, physiological monitors, monitors suitable for monitoring the cardiac output, personal computers, hospital management systems), as well as providing audio/video data (e.g., Video Out, Component Video, S-Video, HDMI, VGA, DVI, RGB) in various data formats (e.g., MPEG, JPEG, etc.) for connecting to the display device 99 or other display devices (display screens, monitors, tablet PCs) are possible by means of the interface 91. The calculation and control unit 70 performs a plurality of tasks within the arrangement 10, such as the coordination with the data input unit 50 and with the data output unit 90. The calculation and control unit 70 is designed in a preferable and exemplary manner as a central processing unit (CPU, μP (microprocessor)) or arrangement of individual microcontrollers (μC). The calculation and control unit 70 comprises additional units, which are designed for the further processing, storage and preparation of the EIT data 3, 3', 4, 5. Thus, a separation unit 73, a first synchronization unit 75, an optional second synchronization unit 77, a processing unit 79, as well as a data memory 74 are provided. As an additional component, a memory organization unit 79' is integrated into the processing unit 79. Moreover, the arrangement 10 includes various elements for supplying voltage and energy, which are not, however, shown in this FIG. 1. The connections between the elements and units of the arrangement 10 are only shown schematically in this FIG. 1; for example, the essential data links and data inputs and data outputs are shown, but, for the sake of clarity, no supply lines and not all connection lines between the elements and units to one another are shown.

These units may be designed as individual elements of the calculation and control unit 70; however, it is included, in the sense of the present invention, that the calculation and control unit 70 may be divided into other partial modules, as well as be designed by programming to provide the functions of the separation unit 73, of the first synchronization unit 75, of the optional second synchronization unit 77, of the processing unit 79 or of the memory organization unit 79' with the same effect, as described concerning FIG. 1, in an identical or modified sequence of processing.

The data memory 74 is designed, for example, as an array of RAM memory components, data sets and quantities of data sets and also results or interim results of the data processing (calculations, sortings, assignments) to store for the execution of the data processing and to organize jointly with the memory organization unit 79'.

Moreover, a data processing unit 89 is provided, which in this FIG. 1 is designed as a component of the data output unit 90; in an alternative embodiment it is also included in the sense of the present invention that the data processing unit 89 may be designed as a component of the calculation and control unit 70 or distributed to the data output unit 90 and the calculation and control unit 70.

The separation unit 73 further processes the EIT data 3, 3', 4, 5, such that the EIT data 3, 3', or the EIT perfusion data 4 and the EIT ventilation data 5 are distinguished and organized for the further processing into a first quantity of data 501 on perfusion CPRS data sets and into a second quantity of data 502 on ventilation VRS data sets. The separation unit 73 prepares the further processing preferably by means of a distribution and organization of the separated PRS and VRS data sets in different memories of the memory unit 74 by means of the memory organization unit 79'.

In the subsequent further processing, associated perfusion phase information 601 is determined in the first synchronization unit 75 on the basis of the first quantity of data 501 on perfusion CPRS data sets. The perfusion of various regions of the lung takes place with different time delays. If the contraction (systole, recognizable in the ECG based on the so-called R wave) of the heart is taken as a beginning of the flow of blood to the lung, then the blood spreads out from the pulmonary artery into various regions of the lung at different rates. The perfusion phase information 601 represents these physiological conditions as additional information to the first quantity of data 501 on perfusion CPRS data sets. The perfusion phase information 601 indicates thereby in which phase position the perfusion data sets of various regions of the lung relate to one another or relate to a reference point in time (for example, the flowing of blood into the pulmonary artery or the R wave in the ECG). Based on the perfusion phase information 601, all perfusion data sets of the first quantity of data 501, based on CPRS, are subsequently synchronized to one another in the first synchronization unit 75 and a third quantity of data 503, based on synchronized perfusion or sCPRS data sets is formed from this.

In a subsequent optional further processing, associated ventilation phase information 602 is determined based on the second quantity of data 502 on ventilation or VRS data sets in the optional second synchronization unit 77. The ventilation of various regions of the lung takes place with different time delays. The ventilation phase information 602 thereby indicates in which phase position the ventilation data sets of various regions of the lung relate to one another or relate to a reference point in time. The ventilation phase information 602 is made available by the optional second synchronization unit 77 via the data processing unit 89 to the data output unit 90. On the basis of the ventilation phase information 602, all ventilation data sets of the second quantity of data 502—VRS—are subsequently synchronized to one another in the optional second synchronization unit 77 and a fourth quantity of data 504 based on synchronized ventilation data—sVRS data sets—is formed from this.

In an alternative embodiment of the arrangement of functional elements 10, the sequence of the processing of separation and synchronization in the calculation and control unit 70 may be designed as exchanged with each other, such that the separation unit 73 is arranged in connection to the first and/or second synchronization unit 75, 77.

In an optional, further, subsequent processing of the ventilation data, the fourth quantity of data 502 based on synchronized ventilation data—sVRS data sets—is matched to the third quantity of data 503 based on synchronized perfusion data—sCPRS data sets—in the processing unit 79, and a fifth quantity of data 505 based on synchronized ventilation data—sVRS' data sets—is thus formed. The fifth quantity of data 505—sVRS'—is matched thus to the third quantity of data 503—sCPRS—in relation over time. Because of the markedly different heart rate ranges (adults: 100±40 bpm; infants: 130±40 bpm), and respiration rate (adults: 12-15 breaths per minute; infants: approximately 25 breaths per minute), as well as the statistically random time variability of the heart rate and because of the statistically random time variability of the respiration rate independent thereof, a long-lasting complete synchronization of perfusion data and ventilation data cannot be achieved, but rather only a matching.

However, with this matching, it is possible to achieve that the ventilation data of the fifth quantity of data 505 based on synchronized ventilation data—sVRS' data sets—and the perfusion data of the third quantity of data 503 based on synchronized perfusion data—sCPRS data sets—are provided by the data output unit 90 and/or the data processing unit 89 in a form, which makes essentially synchronized, uniform or simultaneous forms of visualization between ventilation and perfusion on the display device 99 possible.

Synchronized or simultaneous visualization of perfusion and ventilation requires a synchronization with phase determination of the perfusion data. The synchronization within the ventilation data 502—VRS—to provide synchronized ventilation data 504—sVRS—, or their matching over time to the perfusion data based on sVRS', offers advantages in the further processing and visualization, since further computing operations can then take pace with the data sets with a standardized time reference.

The third quantity of data 503 based on synchronized perfusion—sCPRS data sets—is differentiated in the processing unit 79 by means of a further analysis of the perfusion phase information 601 into an eighth quantity of data 508—sPRS—based on data sets with assignment to lung perfusion and into a ninth quantity of data 509—sCRS—based on data sets with assignment to heart perfusion/heart filling level. The perfusion phase information 601 is made available by the first synchronization unit 75, the processing unit 79 and via the data processing unit 89 to the data output unit 90. A further data processing of the third quantity of data 503—sCPRS—, or of the eighth quantity of data 508—sPRS—and the ninth quantity of data 509—sCRS—based on data sets into phase-related data compilations 98, is carried out in the processing unit 79 or the data processing unit 89 based on the perfusion phase information 601. These phase-related data compilations 98 may be used in the further processing, for example, for a designing of visualization variants (FIGS. 3b-3d, FIGS. 4a-4d). The phase-related data compilations 98 make possible synchronized forms of visualizations of the perfusion of the lung 508 (sPRS) and/or of the heart 509 (sCRS). An embodiment variant of such phase-related data compilations 98 is an essentially synchronized visualization form of one or more blood exchange cycles (blood inflow/blood outflow) of the lung synchronously with one or more blood exchange cycles (blood inflow/blood outflow) of the heart.

Thereby, in a first variant (sPRS & sCRS in phase; 0° variant), the blood exchange in the lung and heart is shown in an in-phase synchronized manner in a shared sPRS/sCRS image. As an alternative to this, in a second variant (sPRS & sCRS in opposition, 180° variant), the blood exchange in the lung and heart may be shown in an in-opposition synchronized manner in a shared sPRS/sCRS image, such that the perfusion of the lung and the perfusion of the heart are alternately visible in the display. The visualization may thereby preferably take place in the form of individual images, sequence of individual images or in the form of an essentially continuous sequence of images or as a film. Thereby, for example, a false color visualization is used for the graphic coding of the data, whereby perfusion data are shown in a first red color spectrum in a preferable and exemplary manner and ventilation data are shown in a blue color spectrum in a preferable and exemplary manner.

In the further subsequent processing, in the processing unit 79, the second quantity of data 502 based on ventilation data sets or the fourth quantity of data 504 based on synchronized ventilation—sVRS—or the fifth quantity of data 505 based on synchronized ventilation data—sVRS' data sets—is set into a ratio to the third quantity of data 503 based on synchronized perfusion—sCPRS—or to the eighth quantity of data 508 based on synchronized perfusion data—sPRS data sets—, and a sixth quantity of data 506 based on synchronized V/Q (sV/Q) parameters is formed. For this purpose, preferably the ratio of ventilation-related signals 502, 504 and perfusion-related signals 503, 508 is formed for each individual lung region, such that a related parameter is obtained for individual lung regions, from which it is recognizable what condition this respective lung region has regarding ventilation and perfusion. The sixth quantity of data 506 based on synchronized V/Q (sV/Q) parameters is provided by the data output unit 90.

Besides the determination of the sixth quantity of data 506 on synchronized V/Q (sV/Q) parameters, an additional global parameter is optionally determined in the processing unit 79 from the sixth quantity of data 506 based on synchronized V/Q parameters as a global sV/Q characteristic value 510, which characterizes the condition of the entire lung regarding ventilation and perfusion.

This global sV/Q characteristic value 510 is obtained, for example as a median $sV/Q_{Median}$ or mean value $sV/Q_{Mean}$ 510 of all parameters from the sixth quantity of data 506 on synchronized V/Q (sV/Q) parameters.

Besides the global characteristic value $sV/Q_{Global}$ 510 as mean value ($sV/Q_{Median}$, $sV/Q_{Mean}$) 510 over all regions of the lung, it is, moreover, advantageous to optionally determine a minimum value $sV/Q_{Min}$ 510', as well as also a maximum value $sV/Q_{Max}$ 510" from the sixth quantity of data 506 based on synchronized V/Q (sV/Q) parameters in order to standardize, for example, the sixth quantity of data 506 based on synchronized V/Q parameters thereto for further processing, providing or visualization.

A distinction into, for example, four constellations A (lung regions with sufficient ventilation and with sufficient perfusion, B (lung regions with sufficient ventilation and insufficient perfusion), C (lung regions with insufficient ventilation and with sufficient perfusion) and D (lung regions with insufficient ventilation and with insufficient perfusion) is preferably made in the data output unit 90 and/or the data processing unit 89 on the basis of the sixth quantity of data 506—sV/Q—and provided to the data output unit 90. This providing of these four constellations A-D to the data output unit 90 makes possible, for example, on the display device 99, a graphically coded output, e.g., in the form of a combined lung/heart graph 99', whereby four different colors may be assigned to these four constellations therein.

Figure 4A:
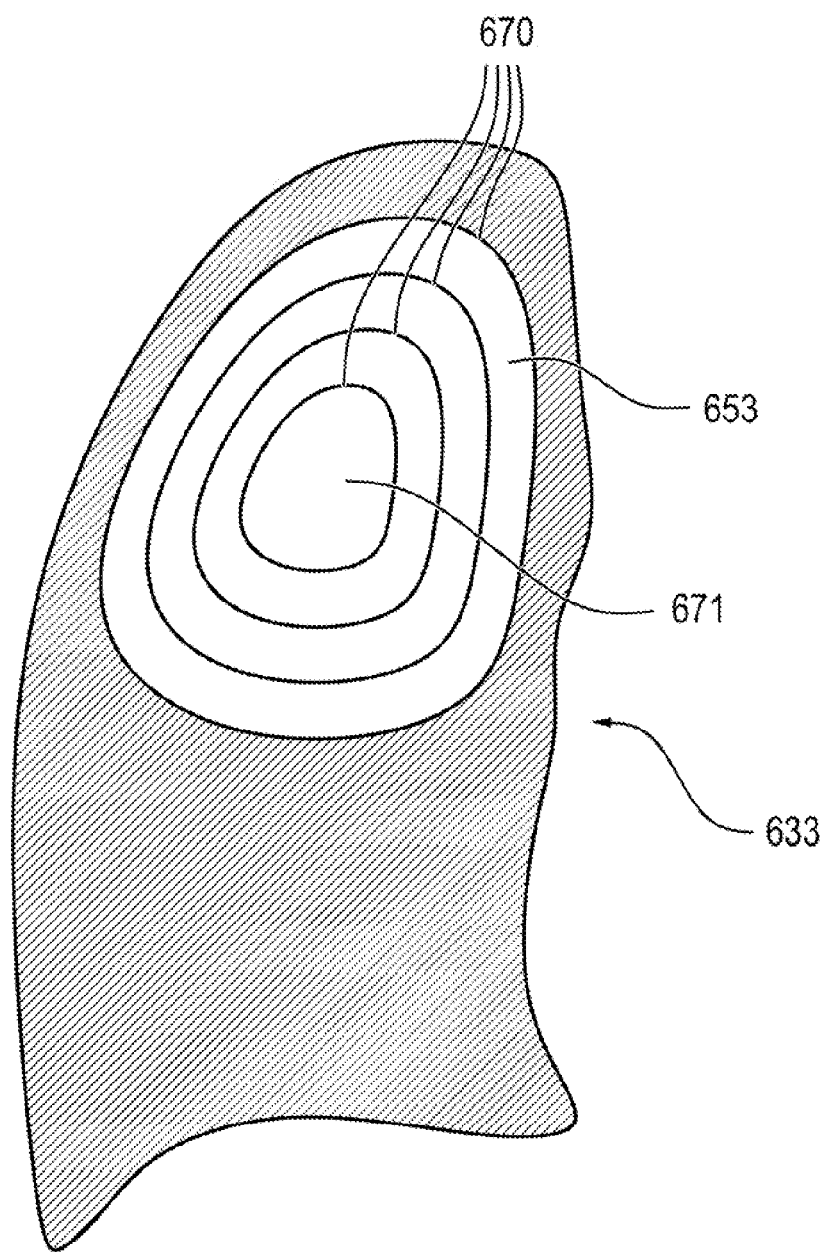
FIG. 4a is a view of various visualization codes.
Figure 4B:
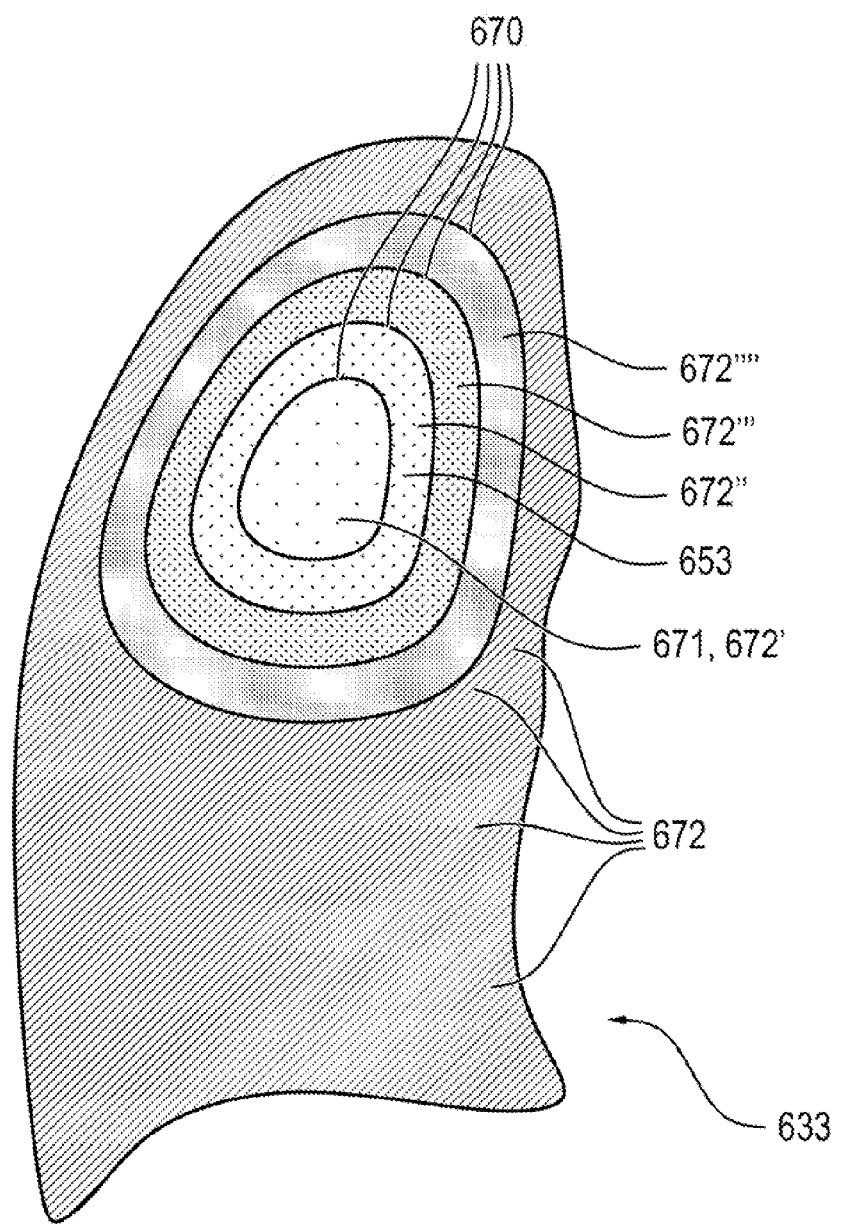
FIG. 4b is a view of various visualization codes.
Figure 4C:
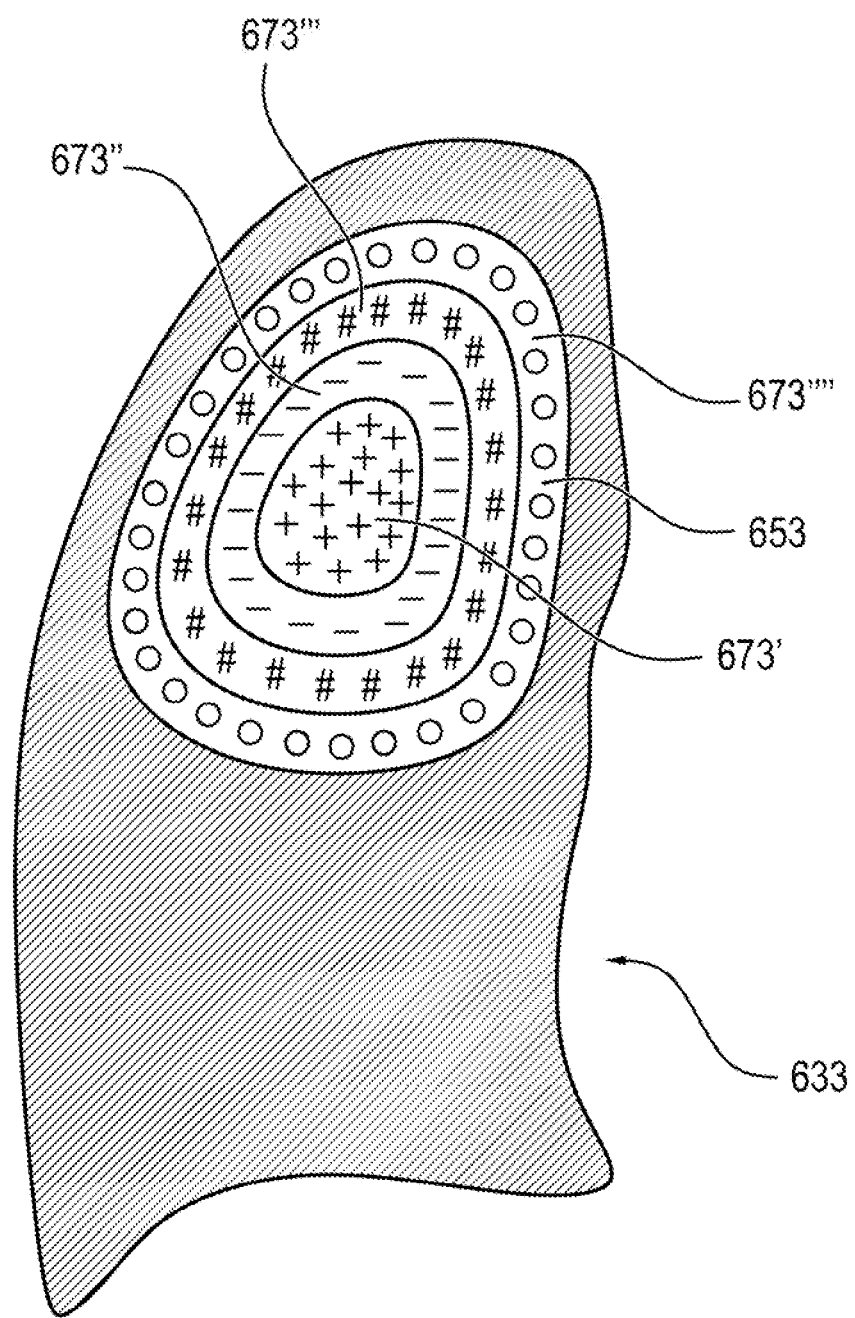
FIG. 4c is a view of various visualization codes.
Figure 4D:
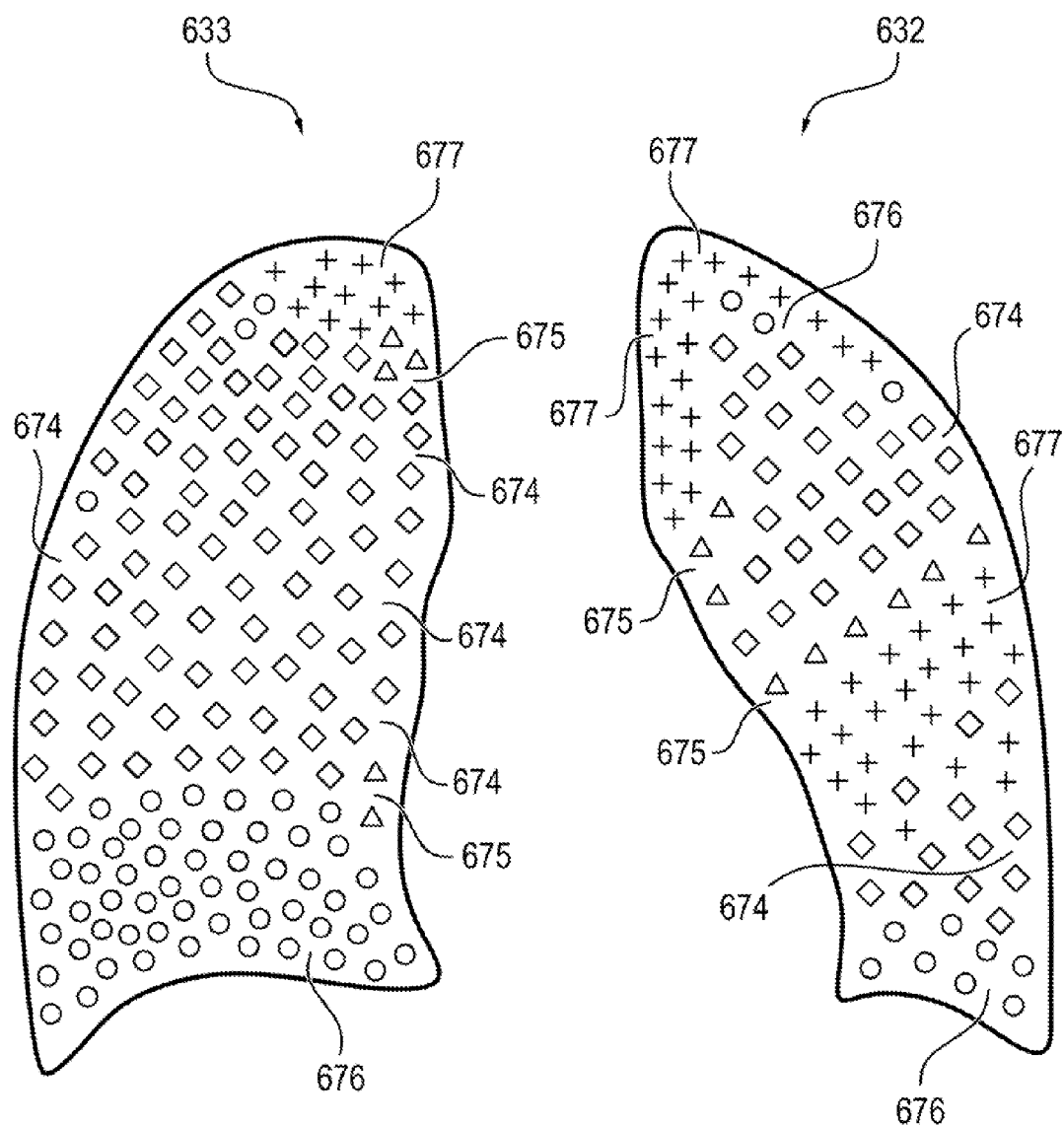
FIG. 4d is a view of various visualization codes.

For this, the following assignment may be mentioned as an example:
constellation A: green
constellation B: blue
constellation C: red
constellation D: gray In addition to this, FIG. 4d schematically shows for a left and a right lung how such a graphically coded visualization based on the four constellations can be converted in an exemplary manner to the synchronized V/Q parameters 506 in the lung/heart graph 99'. For the assignment into one of the four constellations A-D, it is advantageous to standardize the parameters of the sixth quantity of data 506 on synchronized V/Q parameters in each case to a global $sV/Q_{Global}$ characteristic value (FIG. 2b), for example, to the median value $sV/Q_{Median}$, mean value $sV/Q_{Mean}$ 510, minimum value $sV/Q_{Min}$ 510' or maximum value $sV/Q_{Max}$ 510".

In a special visualization variant, ventilation and perfusion are shown jointly. Thus, for example, a plurality of blood exchange cycles (blood inflow/blood outflow) in the lung are matched as a mean blood exchange cycle over time to the breathing cycle (inspiration/expiration), such that in a first variant the perfusion of the lung and the ventilation of the lung (V & Q in phase, 0° variant) are displayed in a joint VQ image. Here, a false color visualization is preferably used for the graphic coding of the data, whereby the perfusion data are preferably shown in a red color spectrum and the ventilation data are preferably shown in a blue color spectrum. An alternative visualization form represents as a second variant (V & Q in opposition; 180° variant) of a VQ image the mean blood exchange cycle in exchange with the breathing cycle, such that alternately the ventilation is shown in the blue color spectrum in a preferable and exemplary manner and the perfusion is shown in the red color spectrum in a preferable and exemplary manner in the rhythm of breathing.

As an alternative to the false color visualization with colors, graphic codes based on gray shades or patterns, for example, shading are also included in the sense of the present invention.

Local phase indices are determined in the processing unit 79 from the third quantity of data 503 based on synchronized perfusion—sCPRS—or from the eighth quantity of data 508 based on synchronized perfusion—sPRS data sets—or from the first quantity of data 501—CPRS—for individual regions of the lung and combined in the form of a seventh quantity of data $phase_{index}$ 507 based on phase position-indexed perfusion data sets.

The data processing unit 89 processes the seventh quantity of data 507—$phase_{index}$—in such a way that data sets with the same local phase index or with a local phase index in a preset tolerance range of the same local phase index are combined into groups in phase-related data compilations 98.

Based on the processing of the seventh data quantity 507 $phase_{index}$ into local phase indices, it is possible to provide phase-related data combinations 98 to the data output unit 90 at the interface 91. Special regions of interest (ROI=Region Of Interest) 620 (FIG. 3b) can be formed for the lung and also for the imaging of the lung in the form of an EIT visualization based on the phase-related data compilations 98. Thus, the associations with groups based on the local phase index can be used as criteria for the formation of such special regions of interest (ROI) 620 (FIG. 3b).

The regions of the lung combined into special regions of interest (ROI) 620 (FIG. 3b) are thereby preferably shown with a similar graphic visualization code on the display device.

The grouping into special regions of interest (ROI) 620, 621 (FIGS. 3b, 3c) produces an image of the lung with spatial division combined with time-related information on perfusion. As an example, it can be mentioned here that a quantity of data of the smallest blood vessels (capillaries) in the lung could be of interest as a special region of interest (ROI). The plurality of the smallest capillaries has an increasing time offset (phase difference) to the blood inflow at the pulmonary artery, the further removed from the pulmonary artery they are. Thus, the quantity of data of the smallest blood vessels over the phase-related data compilations 98 (FIGS. 3b, 3c) can be defined as a special region of interest (ROI) 620, 621 (FIGS. 3b, 3c). The aorta, the pulmonary artery, the lesser lung circulation (vasa publica) and the variable lung circulation (vasa privata) for supplying the lung, with the right ventricle and pulmonary artery and left ventricle and pulmonary vein or even the coronary vessels for supplying the myocardium can be mentioned as further examples of special regions of interest (ROI).

The determination, compiling or providing of a variable corresponding to the pumping capacity of the heart or the regional perfusion of the heart can be mentioned as a further example of a phase-related data compilation 98 based on the synchronized perfusion data sets (sCPRS, sCRS, sPRS). Variables corresponding to the pumping capacity of the heart are, for example, the cardiac output. Since the quantity of blood of the human body flows due to the pumping capacity of the heart in the exchange between the heart and the lung, a first indicator of the quantity of blood, which altogether flows back from the lung to the heart as a variable corresponding to the pumping capacity of the heart, is obtained, on the one hand, from the eighth quantity of data 508 based on synchronized perfusion sPRS data sets by taking into account the perfusion in the lung altogether in a defined time interval (heart rate cycle, filling phase, diastole).

A second indicator of the quantity of blood, which flows out from the heart as ejection fraction as a further variable corresponding to the pumping capacity of the heart, is obtained from the ninth quantity of data 509 based on synchronized cardiac data—sCRS data sets—by taking into account the perfusion of the heart region in a defined time interval with the next contraction, or systole (heart rate cycle: R wave-T wave).

Since the quantity of blood flowing from the lung to the heart is in balance with the quantity ejected by the heart without a blood loss of the patient, the ejection fraction of the heart can be indirectly determined both from the first indicator determined by means of the eighth quantity of data 508 based on synchronized perfusion data—sPRS data sets—and from the second indicator determined by means of the ninth quantity of data 509 based on synchronized cardiac data—sCRS data sets. Thus, an indirect variable, which is in connection with the ejection fraction of the heart, also known as cardiac output (CO), is possible in a non-invasive manner by means of the EIT both from the first and from the second indicator. The analysis of the EIT data and the synchronization of the perfusion data thus represent an alternative to invasive methods, for example, thermodilution by means of intravenous injection and central venous catheter or even semi-invasive methods, such as pulse contour analysis. Non-invasive methods cause physically markedly less discomfort for the patient and are connected with fewer possibilities of complications and risks regarding hygiene (bacterial transmission) and thus are to be preferred over invasive methods. The first and second indicators are well suited for a non-invasive long-term monitoring; since electroimpedance tomography can detect only impedances of the tissue, as well as gases and blood contained therein; however, a calibration or standardization is helpful in order to derive absolute values of the cardiac output therefrom. Combined with a non-invasive administration of a defined bolus of a saline solution or with methods of thermodilution, the period of observation can be designed as suitable for data acquisition or data analysis over time and thus the statement of the first as well as of the second indicator can be improved.

The data output unit 90 makes available, by means of the interface 91, the first quantity of data—CPRS data sets 501, the second quantity of data—VRS data sets 502, the third quantity of data—sPRS data sets 503, the fourth quantity of data—sVRS data sets 504, the fifth quantity of data—sVRS' data sets 505, the sixth quantity of data 506—sV/Q parameters, the seventh quantity of data 507—phase$_{index}$, the eighth quantity of data 508—sPRS, the ninth quantity of data 509—sCRS, the global sV/Q characteristic value 510, the data compilation 96, the phase-related data compilations 98, as well as the perfusion phase information 601 and the ventilation phase information 602, for example, to the display device 99 and also outside of the arrangement 10 to the various external devices 200 or the data network 300.

An optional input and control unit 80 (shown with dotted line in this FIG. 1) is provided, which is suited or designed for a parametrization or a configuration of the calculation and control unit 70 and/or of the data output unit 90 or of the data processing unit 89. For connecting the optional input and control unit 80 to the calculation and control unit 70, an optional first configuration unit 78 is provided in the calculation and control unit 70. An optional second configuration unit 88 is also provided in the data processing unit 89 (as a component of the data output unit 90) for connecting the optional input and control unit 80 to the data output unit 90. With the parametrization or the configuration, for example, the manner of shaping the regions of interest (ROI) can be influenced based on the phase position by the phase tolerance ranges for the grouping of the perfusion data and/or the indexing being able to be defined. A manner of averaging (a number of breathing cycles, a sliding mean value, a median filtering, a frequency filtering, a 50/60 Hz and noise suppression), a design of the graphic coding of the visualization on the data output unit 90, such as color settings of the ROI (gray values, false color spectrum, shading), manner of synchronized visualization (180° variant, 0° variant) of ventilation and perfusion, standardization of perfusion and ventilation, e.g., to one of the global mean values, to minimum and maximum values, standardizations as to the type of patient (lung volume correlated with height, body weight, gender, age, clinical pictures) are further configuration possibilities. Moreover, also standardizations or visualization variants for special clinical pictures, such as COPD, ARDS, which may influence the function of the calculation and control unit 70 and/or the data output unit 90 by means of the optional input and control unit 80 may be provided.

Figure 2A:
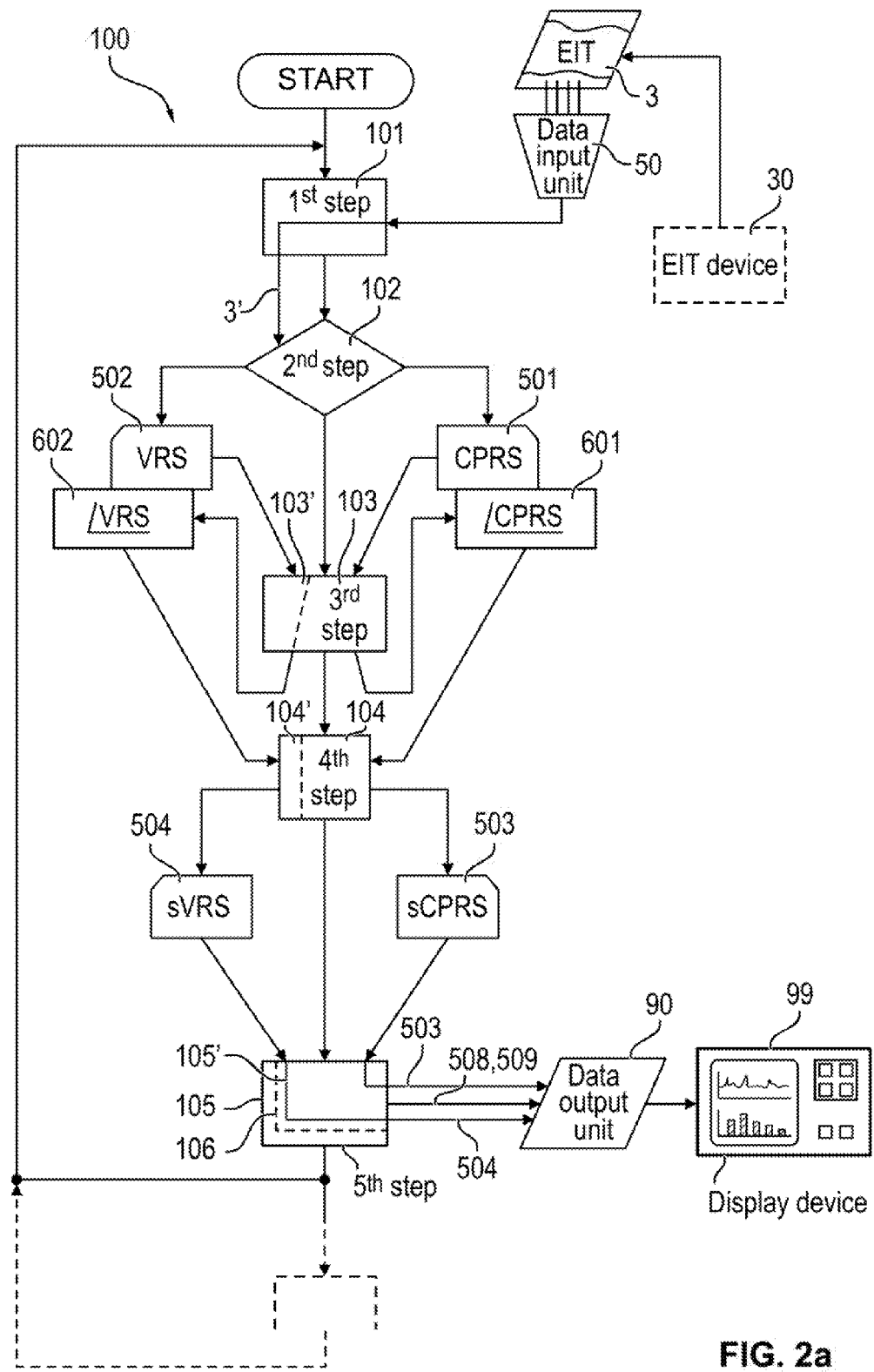
FIG. 2a is a schematic flow chart for the processing of EIT data.

FIG. 2a schematically shows an embodiment of a method for processing EIT data in the form of a flow chart 100. Identical elements in FIG. 2a as in FIG. 1 are designated in FIG. 2a with the same reference numbers as in FIG. 1. In this embodiment according to FIG. 2a, the EIT data are preferably present as a total quantity of EIT image data, i.e., data sets determined from the raw data with a reconstruction algorithm, which reproduce local impedances, impedance differences or impedance changes. The method for processing EIT data 3 is now explained in detail by means of a sequence of steps 101-105.

In a first step 101, EIT data 3 are read in. The EIT data 3 are, for example, provided as data sets by an EIT device 30. The EIT data 3 comprise impedance values of the lung, regions of the lung and of the heart of a human body, which were obtained by means of an electroimpedance tomography device. After the reading in, the EIT data are present either in unchanged format as EIT data 3 or in adapted form as EIT data 3' for further processing in subsequent steps.

In a second step 102, the EIT data 3 are distinguished into a first quantity of data 501—perfusion data sets CPRS and into a second quantity of data 502—ventilation data sets VRS. The distinction takes place thereby by means of frequency-selective methods (FFT, ECG gating) on the basis of ECG-based triggered methods or with statistical or model-based mathematical methods, such as principal component analysis (PCA) or independent component analysis (ICA).

In another preferred embodiment variant of the method for the processing of EIT data, in which the EIT data 3' may already be present or read in as data or data sets separated into perfusion data—CPRS—and ventilation data—VRS—, the second step of distinction can be designed in a simplified manner as a data organization into the two quantities of data 501 and 502. In a third step 103, perfusion phase information 601 of the first quantity of data 501, of the perfusion data sets CPRS, are determined together.

In an optional expanded embodiment of the third step 103 (shown as a partial function block 103' separated with dotted line in FIG. 2a), additional pieces of ventilation phase information 602 of the second quantity of data 502 of the ventilation data sets VRS are determined together. The phase information 601 or 602 is determined in the third step 103 or 103', respectively, based on a phase analysis in the frequency range or based on a cross correlation.

A third quantity of data 503 on synchronized perfusion sCPRS data sets is determined in a fourth step 104 from the phase information 601 determined and from the first quantity of data 501 of the perfusion CPRS data sets. In an optional expanded embodiment—shown as a partial function block 104' separated with dotted line in this FIG. 2—of the fourth step 104, a fourth quantity of data 504 on synchronized ventilation sVRS data sets is additionally determined from the phase information 602 determined. The synchronization of the data sets of the first quantity of data 501—CPRS—or of the second quantity of data 502—VRS—to synchronized data sets 503—sCPRS—or 504—sVRS, respectively, takes place based on a phase adaptation in the frequency spectrum or based on a shift of individual data sets in the time period. The synchronized perfusion data sets may preferably be further distinguished by means of the phase information 601 into an eighth quantity of data on synchronized data sets sPRS 508 with assignment to cardiac perfusion.

The third quantity of data 503 sCPRS, the eighth quantity of data 508 sPRS or the ninth quantity of data 509 sCRS on synchronized perfusion data sets is provided in a fifth step 105. In another preferred, expanded embodiment—suggested as an embedded partial function block 105' in this FIG. 2a—the fourth quantity of data 504 on synchronized ventilation sVRS data sets is provided additionally in the fifth step 105. In an optional sixth partial step 106 within the fifth step 105—shown in FIGS. 2a, 2b, 2c in dotted line—the third quantity of data 503 on synchronized perfusion sCPRS data sets or/and the fourth quantity of data 504 on synchronized ventilation sVRS data sets are each separately outputted via a data output unit 90 in a synchronized graphic visualization manner in individual images or in a shared image, for example, on a display device 99. This process 100 is continuously repeated as a sequence of steps of the steps 101, 102, 103, 104, 105, as well as optionally also for the optional step 106, so that EIT data 3 are continuously read in and are provided as synchronized data sets 503, optionally 504, 508, 509.

Figure 2B:
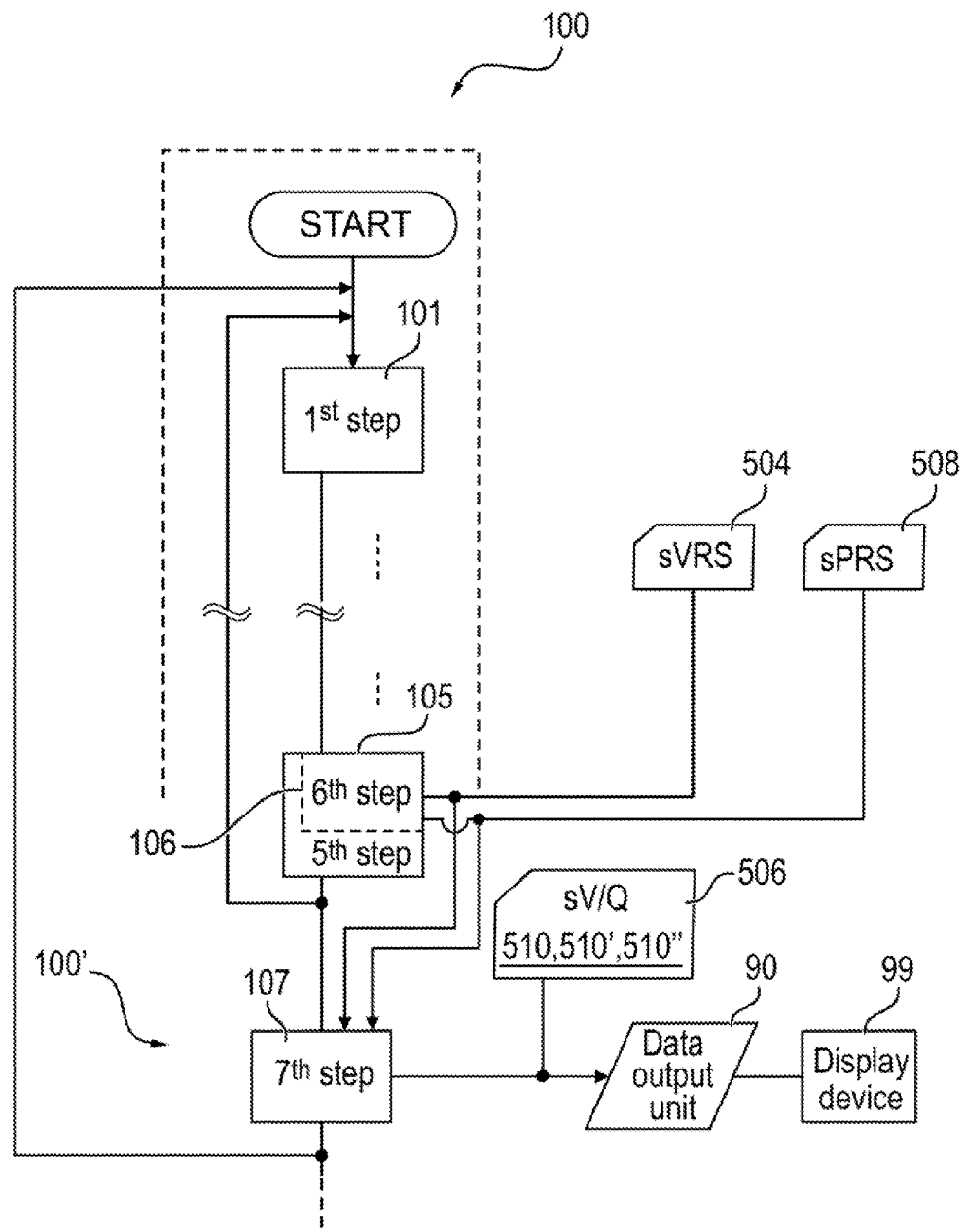
FIG. 2b is a schematic flow chart for the processing of EIT data.
Figure 2C:
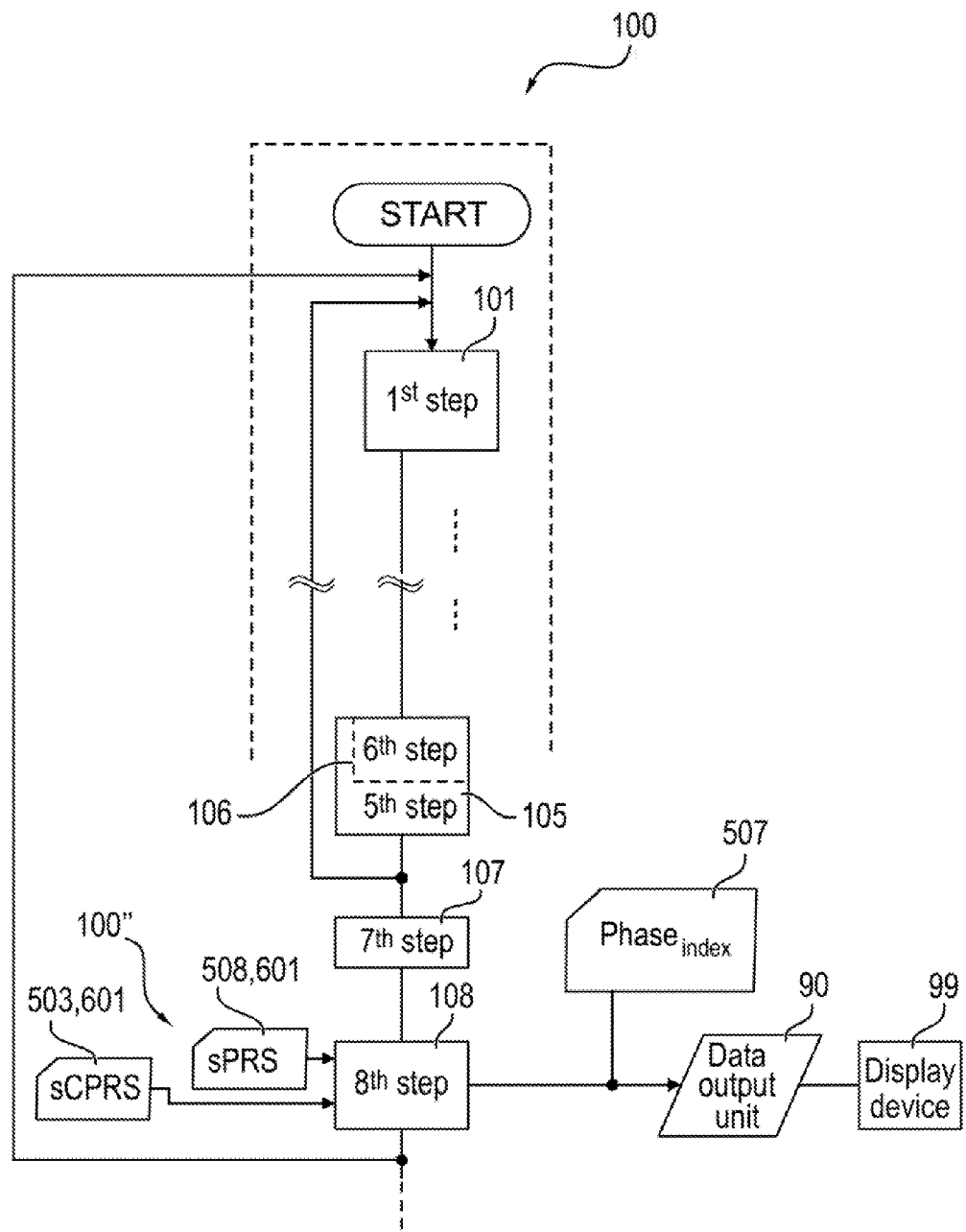
FIG. 2c is a schematic flow chart for the processing of EIT data.

Optional further steps for further processing output and visualization are connected to this process 100 for processing EIT data 3, 3' or they are added in this continuous process 100, which are now described in detail based on FIGS. 2b and 2c. Identical elements in the figures, e.g., 2c as in FIGS. 1 and 2a are designated with the same reference numbers in the figures, e.g., 2c as in FIGS. 1 and 2a.

After providing the fourth quantity of data 504—sVRS—and the eighth quantity of data 508—sPRS—in the optional sixth step 106, a sixth quantity of data based on sV/Q parameters 506 is, as is apparent from FIG. 2b, determined in the process 100' in a further (seventh) step 107 from the fourth quantity of data 504—sVRS—and from the eighth quantity of data 508—sPRS—and outputted via the data output unit 90 on the display device 99. Global sV/Q characteristic values in the form of a mean characteristic value $sV/Q_{Mean}$, $sV/Q_{Median}$ 510, as minimum and as maximum characteristic values $sV/Q_{Min}$ 510', $sV/Q_{Max}$ 510" are determined as the sixth quantity of data on sV/Q parameters 506 and outputted via the data output unit 90 on the display device 99. For the visualization, it is advantageous to standardize the sixth quantity of data 506 on sV/Q parameters to one of these global sV/Q characteristic values 510, 510', 510" in order to be able to clearly illustrate even slight regional differences in perfusion and ventilation in the lung in the visualization.

It is shown in FIG. 2c how further steps for the further processing of the EIT data 3, 3', as well as for the further processing of the data sets 503, 504, 601, 602 are connected to the sequence of steps 101, 102, 103, 104, 105, 106, 107 according to FIG. 2a and FIG. 2b in the process 100". In a further (eighth) step 108, a local phase index is determined, using the phase information 601, from the third quantity of data 503—sCPRS—or from the eighth quantity of data 508—sPRS—based on synchronized perfusion data sets for individual regions of the lung. The respective local phase index is compiled and provided in the form of a seventh quantity of data $phase_{index}$ 507 based on phase position-indexed perfusion data sets and output via the data output unit 90 on the display device 99. Perfusion regions of interest (PR-ROI, Perfusion Related Regions of Interest) are compiled based on the local phase indices of the seventh quantity of data $phase_{index}$ 507. In such a compilation, locations with identical phase position or similar phase position are combined into perfusion-related regions of interest. Such perfusion-related regions of interest can be determined in step 108 on the basis of the phase indices, for example, for heart, lung, pulmonary vein, pulmonary artery, aorta, lesser or variable lung circulation. Further examples and embodiments on perfusion-related regions of interest (PR-ROI) appear from the description to FIG. 1, as well as from the FIGS. 3a, 3b, 3c, 3d as well as regarding the graphic embodiment from FIGS. 4a, 4b, 4c, 4d.

FIGS. 3a, 3b, 3c, 3d schematically show the heart and lung, as well as special regions of interest (ROI) regarding perfusion in a simplified manner. These regions of interest (ROI) regarding perfusion result, for example, from phase-related data compilations 98 (FIG. 1, FIG. 2a). Identical elements in FIGS. 3a, 3b, 3c, 3d are designated with the same reference numbers in FIGS. 3a, 3b, 3c, 3d. Identical elements in FIGS. 3a, 3b, 3c, 3d as in FIGS. 1, 2a, 2b, 2c are designated in FIGS. 3a, 3b, 3c, 3d with the same reference numbers as in FIGS. 1, 2a, 2b, 2c.

Figure 3A:
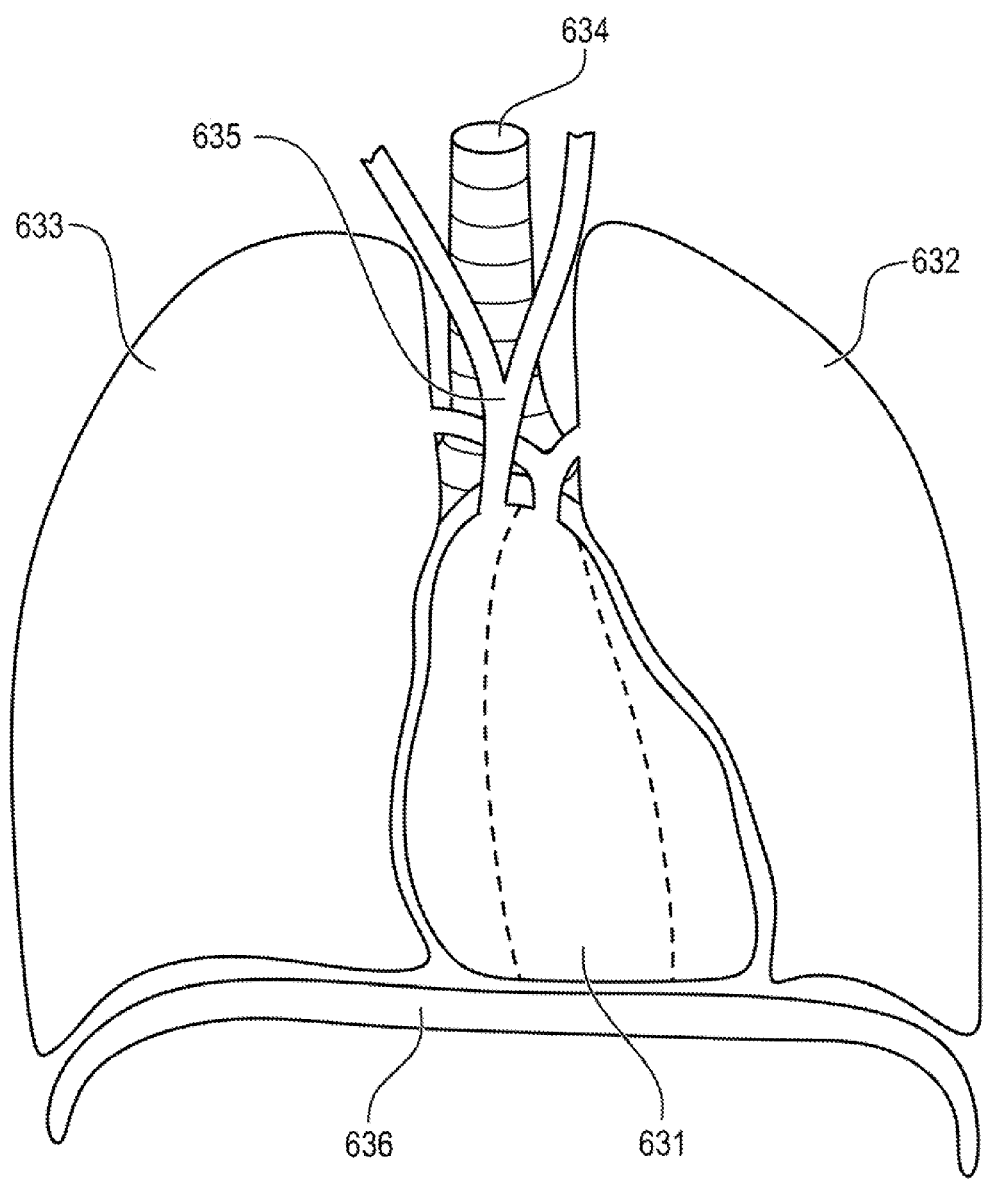
FIG. 3a is a schematic anatomical view of the cardiac-lung region.
Figure 3B:
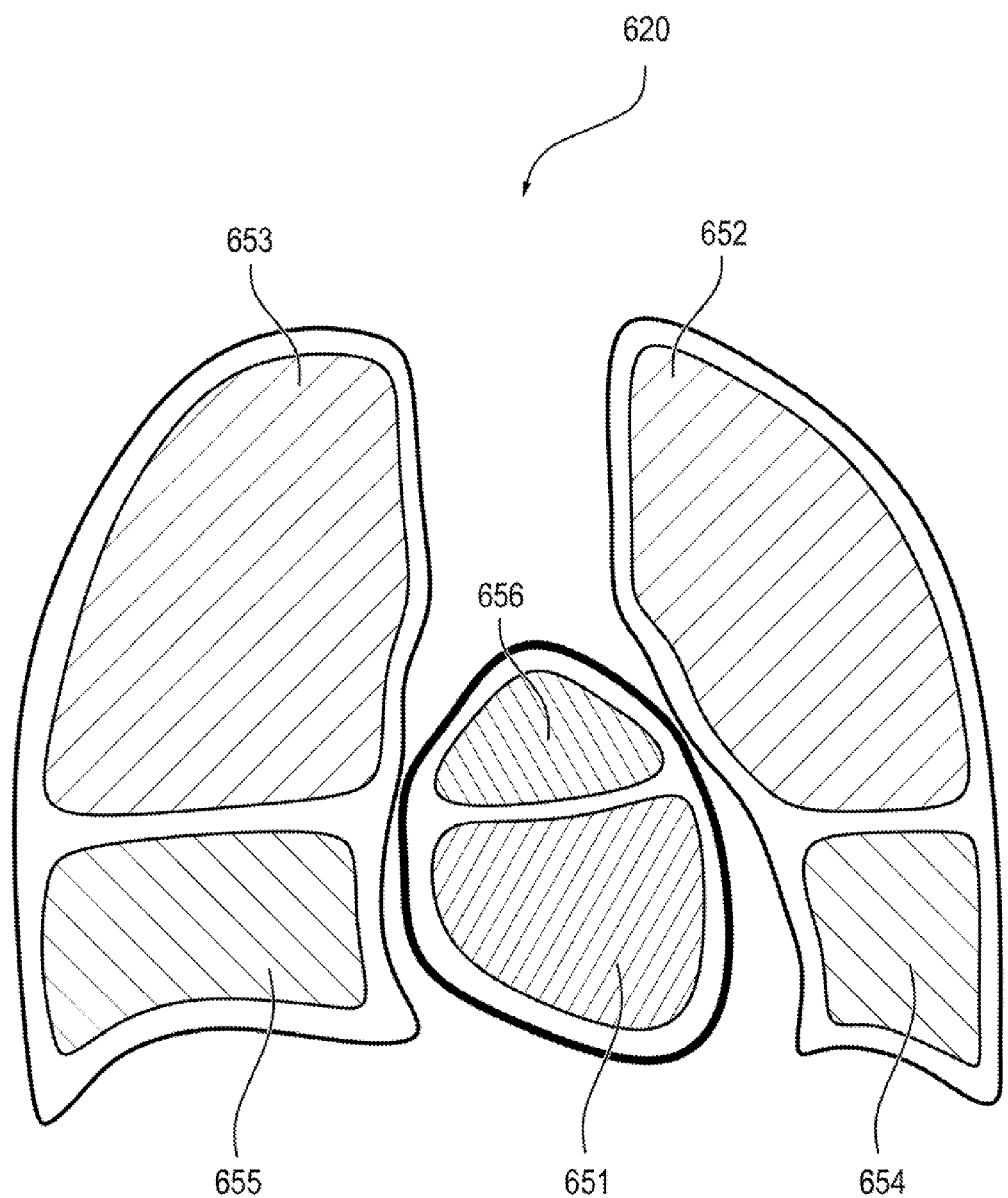
FIG. 3b is a view of EIT data with visualization of special regions of interest in the frontal plane.
Figure 3C:
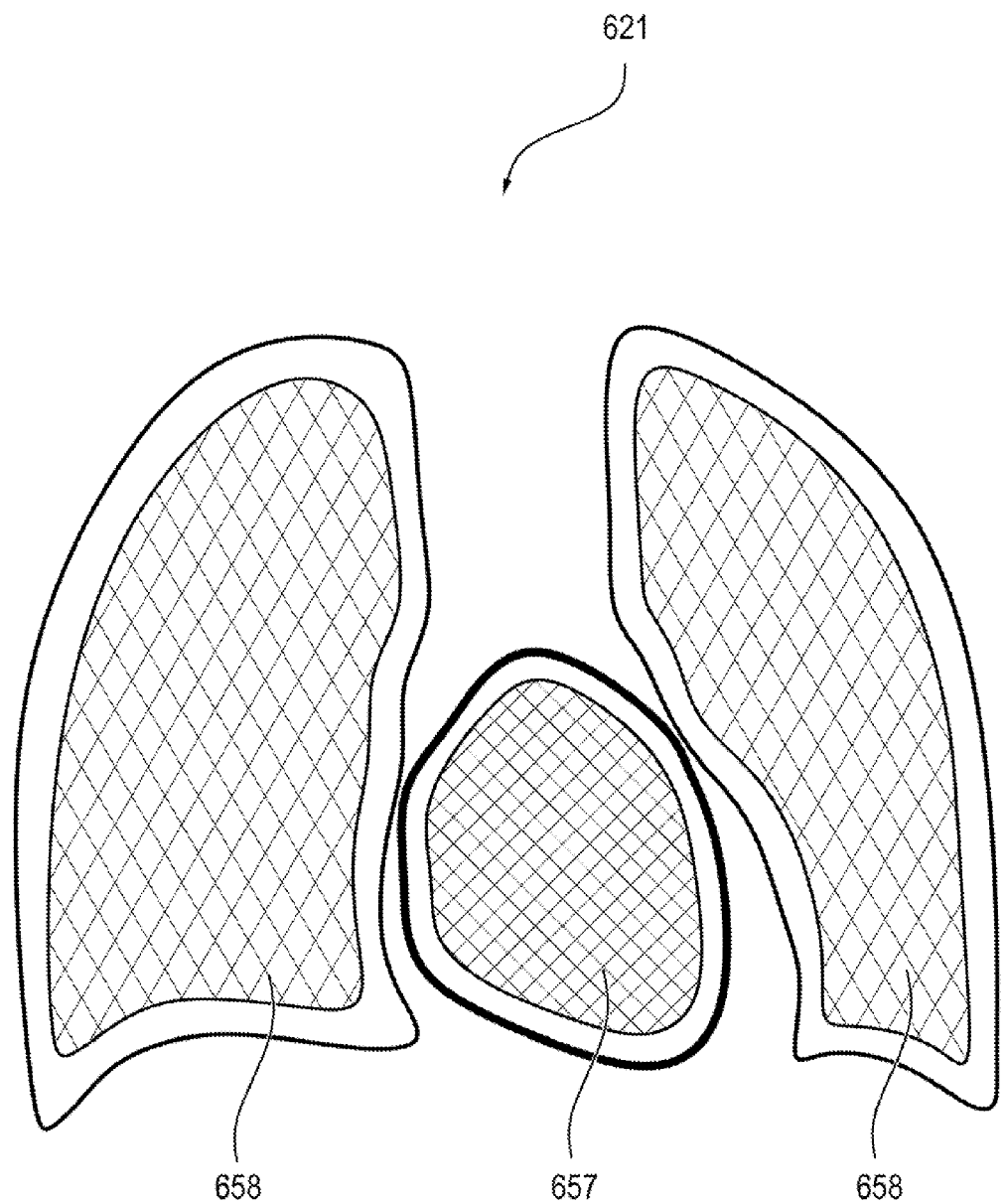
FIG. 3c is a view of EIT data with visualization of special regions of interest in the frontal plane.

FIG. 3a shows in a schematic view the anatomical outlines of the lung and heart with the left and right lung 632, 633, trachea 634 in a two-dimensional shared visualization with the heart 631 and the aorta 635, as well as the diaphragm 636. This schematic view shows the heart and lung in a frontal view. For the sake of clarity, a visualization of elements of the skeleton, such as ribs and vertebrae or other organs is dispensed with, even though these would likewise be recognizable in an imaging by means of X-ray. FIG. 3a shall contribute to the understanding of the following FIGS. 3b, 3c, 3d, 4a, 4b, 4c, 4d.

In FIGS. 3b and 3c, corresponding to the two-dimensional visualization according to FIG. 3a, are shown images of the perfusion in the frontal view obtained from data obtained from a medical device suitable for generating data for imaging (EIT, CT, MRT), in which various special regions of interest (ROI=Regions Of Interest) 620 are illustrated. The special regions of interest are shown in FIGS. 3b and 3c likewise in a frontal view in order to illustrate the relation to the anatomy also in the drawing—shown in frontal view in FIG. 3a. It should be noted here that—unlike X-rays of the thorax—by means of electroimpedance tomography, partly due to the position of the EIT electrodes or computer tomography, partly due to the detection principle of the CT scan, no direct frontal views can be generated, but images in the so-called transversal plane are generated. There are, however, possibilities of later mathematically generating further views in the body plane, such as frontal view or sagittal view from the detected data, for example, in a 3D-CT. A first special region of interest ROI_H1 651 of perfusion shows the region of the heart. A second special region of interest $ROI\_LL_{central}$ 652 of perfusion shows a central region of the left lung. A third special region of interest $ROI\_LR_{central}$ 653 of perfusion shows a central region of the right lung. A fourth special region of interest $ROI\_LL_{downside}$ 654 of perfusion shows a downside region of the left lung. A fifth special region of interest $ROI\_LR_{downside}$ 655 of perfusion shows a downside region of the right lung. A sixth special region of interest ROI_H2 656 of perfusion shows the region of the aorta.

FIG. 3c shows further regions of interest (ROI) 621 derived from the special regions of interest according to FIG. 3b. The second, third, fourth and fifth regions of interest 652, 653, 654, 655 are combined in a seventh special region of interest ROI_L$_{All}$ 657 of perfusion of the lung (FIG. 3b). The first and sixth regions of interest 651, 656 are combined in an eighth special region of interest ROI_H$_{All}$ 658 of perfusion of the heart (FIG. 3b).

Figure 3D:
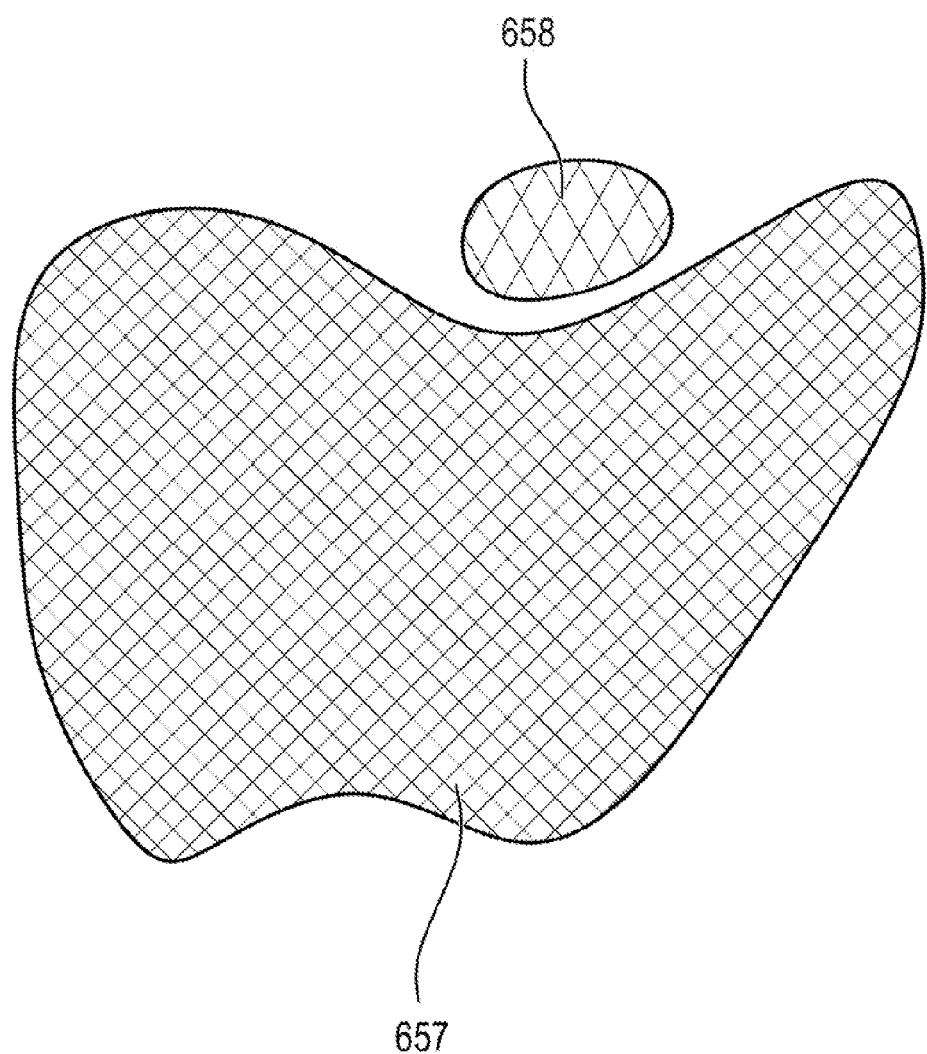
FIG. 3d is a view of EIT data with visualization of special regions of interest in the transversal plane.

The special regions of interest according to FIG. 3c are shown in FIG. 3d in the transversal view in a schematic form not in agreement in terms of scale with FIGS. 3a, 3b, 3c. FIG. 3d shows the seventh special region of interest ROI_L$_{All}$ 657 of perfusion of the lung and the eighth special region of interest ROI_H$_{All}$ 658 of perfusion of the heart in the transversal view.

FIGS. 4a, 4b, 4c, 4d show in the frontal view various visualization codes for the states of perfusion of the lung and heart, as well as of ventilation of the lung, as well as of the ratio of ventilation to perfusion (V/Q), which can be used for illustrating the sPRS data, sCPRS data, as well as VRS data or sVRS, as well as V/Q parameters. Identical elements in FIGS. 4a, 4b, 4c, 4d as in FIGS. 3a, 3b, 3c are designated with the same reference numbers in FIGS. 4a, 4b, 4c, 4d as in FIGS. 3a, 3b, 3c.

The region of interest ROI_LR$_{central}$ 653 corresponding to FIG. 3b is illustrated in FIG. 4a as an exemplary embodiment of a graphic scale with the structure of four exemplary gradient lines 670 for a right lung 633, as it also usual from the visualization of isobars on weather maps or of contour lines on land maps. Such a visualization is advantageous when the variable to be visualized decreases or increases from the middle center 671 outwards. The individual gradient lines 670 show thereby in stepped gradients of the measured variable to be visualized in relation to the center 671. Such a visualization makes possible a coded graphic visualization using essentially monochromatic colors (e.g., red, blue, gray, white, black). The number of four gradient lines is selected here for the sake of clarity in the drawing. The number of two up to ten or more gradient lines is included in the sense of the present invention, whereby the number of gradient lines is usefully essentially adapted to the differences in perfusion between various regions or individual locations of the lung in order to obtain valid graphic coding.

FIG. 4b shows an expansion of the monochromatic visualization according to FIG. 4a by means of a color intensity or transparency variation of the variable to be visualized, whereby the color intensity decreases with the gradient lines from the middle center outwards. If an essentially dark background, e.g., black, is selected, then, with increasing transparency, the intensity of the color decreases from the center outwards; if an essentially light background is selected, then the intensity of the color increases from the center outwards with increasing transparency. For a visualization of the perfusion by means of a color in the red color spectrum against a dark background, a decrease in the color intensity from light red towards gradients to a dark red, scaled with a decrease in perfusion from the center outwards, is then obtained. In this visualization according to FIG. 4b, the degree of transparency or the color intensity is graphically illustrated by means of different point densities of visualized zones in the region of interest ROI_LR$_{central}$ 653. A high point density corresponds here to a low color intensity, a low point density corresponds here to a high color intensity. The gradient lines 670 divide the region of interest ROI_LR$_{central}$ 653 against a background zone 672, shown as shaded, into four exemplary zones of intensity 672', 672'', 672''', 672' with different point densities, with low density corresponding to high color intensity in the center 671, 672' of the region of interest ROI_LR$_{central}$ 653 and gradually increasing point densities corresponding to lower color intensity in the outer zones 672'', 672''', 672'''' of the region of interest ROI_LR$_{central}$ 653.

FIG. 4c shows a further embodiment of a graphic visualization code for the right lung 633 with the region of interest ROI_LR$_{central}$ 653, in which four exemplary zones 673', 673'', 673''', 673'''' of perfusion beginning from the center 671 are distinguished by different shades. In the red color spectrum, a graphic code with the shades dark red, light red, orange and yellow, which are scaled according to the degree of the respective perfusion in the zones 673', 673'', 673''', 673'''' of the region of interest ROI_LR$_{central}$ 653, is obtained for such a visualization in the four exemplary zones. The graphic code by means of the shades is illustrated in this visualization according to FIG. 4c by means of different symbols.

The mathematical "plus" sign (+) corresponds to dark red, the mathematical "minus" sign (−) corresponds to light red, the mathematical "number" sign (#) corresponds to orange, and the "degree" sign (°) corresponds to yellow.

In a special variant of FIG. 4d, the intensity variation according to FIG. 4b is included in the graphic code of FIG. 4c, such that a stepped color pattern, starting from the center 671 outwards, with intensity variations in the individual zones of the region of interest ROI_LR$_{central}$ 653 is obtained in the region of interest ROI_LR$_{central}$ 653. The intensity variation makes possible thereby a sliding transition between the zones of different shades. This special variant may be expanded to a false color visualization as another special variant in the event of including additional shades, as well as brightness or even color saturation. FIG. 4d schematically shows a graphic code for a visualization of the V/Q ratio for a left lung 632 and a right lung 633. A graphically coded visualization of the four constellations A, B, C, D based on the synchronized V/Q parameters 506 (FIG. 1) is carried out in this FIG. 4d by means of an assignment of four different graph symbols to the constellations of perfusion and ventilation 674, 675, 676, 677. As an alternative or in addition, instead of the four graphs symbols, the constellations may be assigned to shades or colors, such as, for instance, green, blue, red, gray, as it is characterized in an exemplary manner in the following list by means of brackets.

Constellation A: Rhombus 674 [green].
Constellation B: Triangle 675 [blue],
Constellation C: Circle 676 [red],
Constellation D: Cross 677 [gray].

Figure 5:
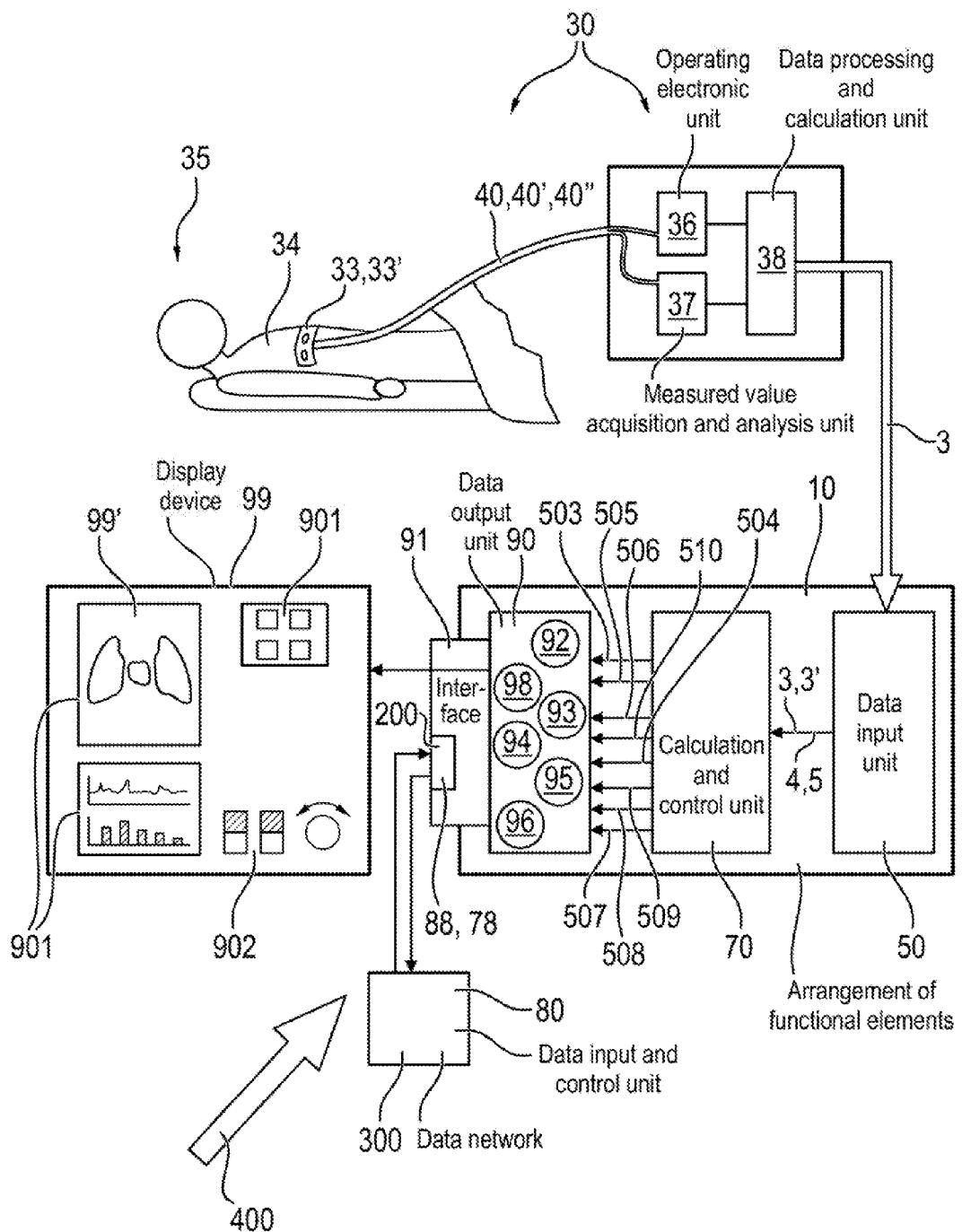
FIG. 5 is a schematic view of a system for detecting, processing and displaying EIT data.

FIG. 5 shows an EIT system 400, comprised of an electroimpedance tomography device 30, an arrangement 10 for the processing of electroimpedance tomography data 3 according to FIG. 1 and a display device 99 according to FIG. 1. Identical elements in FIG. 5 and in FIG. 1 are designated in FIG. 5 with the same reference numbers as in FIG. 1.

The electroimpedance tomography device 30 comprises an electrode array 33 with a plurality of electrodes 33', which is designed, for example, as a belt in this FIG. 5, which is arranged on the thorax 34 of a patient 35, an operating electronic unit 36, which is designed (configured) by means of a supply connection 40' for feeding alternating current or alternating voltage into the electrodes 33', as well as a measured value acquisition and analysis unit 37 for the detection of measured signals at the electrodes 33' by means of a measuring line connection 40''. The supply connection 40' for feeding and the measuring line connection 40'' are embodied as a shared cable in this FIG. 5, but may also be embodied separately. The data processing and calculation unit 38, which is designed by means of processor technology with associated data memory and suitable programming for a process control of the feeding of alternating current/alternating voltage and detection of alternating voltage/alternating current, calculates EIT data 3 from the measured signals of the electrodes 33' by means of a reconstruction algorithm and sends these to the arrangement 10. The arrangement 10 processes the EIT data 3, as described in FIG. 1 and in FIGS. 2a, 2b, 2c, into perfusion quantities of data sCPRS 503, sPRS 508, sCRS 509 and ventilation quantities of data VRS 502, sVRS 504, sVRS' 505, as well as into ventilation/perfusion parameters sV/Q 510, 510' 510" and makes these available by means of the data output unit 90 and sends these as numerical values 95, data sets, data compilations 96 or phase-related data compilations 98 via the interface 91 to the display device 99. The display device 99 visualizes the data numerically, graphically, pictorially by means of the visualization means 901, for example, according to one of the FIGS. 3b, 3c, 4a, 4b, 4c, 4d, preferably in the form of the lung/heart graph 99'. Besides this, the display device 99 comprises various input means 902, such as switches, buttons, knobs or rotary knobs, which are provided and designed for the operation, settings and configuration of the display device 99.

While specific embodiments of the invention have been shown and described in detail to illustrate the application of the principles of the invention, it will be understood that the invention may be embodied otherwise without departing from such principles.

APPENDIX

List of Reference Numbers 3, 3' EIT data
4 Perfusion data
5 Ventilation data
10 Arrangement of functional elements
30 EIT device
40 Cable
40' Supply connection
40" Measuring line connection
50 Data input unit
51 Data input, data inputs
70 Calculation and control unit
73 Separation unit
74 Data memory
75 First synchronization unit
77 Second synchronization unit
78 First configuration unit
79 Processing unit
79' Memory organization unit
80 Data input and control unit
88 Second configuration unit
89 Data processing unit
90 Data output unit
91 Interface
92 Numerical values
93 Images
94 Diagrams
95 Curves, curve courses, signal patterns over time
96 Data sets, data compilations
98 Phase-specific data compilations
99 Display device
99' Lung/heart diagram
100, 100', 100" Flow chart
101 First step
102 Second step
103 Third step
104 Fourth step
105, 105' Fifth step
106 Sixth step
107 Seventh step
108 Eighth step
200 External devices
300 Data network
400 System, EIT system
501 First quantity of data CPRS data sets
502 Second quantity of data VRS data sets
503 Third quantity of data sCPRS data sets
504 Fourth quantity of data sVRS data sets
505 Fifth quantity of data sVRS' data sets
506 Sixth quantity of data sV/Q parameters
507 Seventh quantity of data Phaseindex of the sCPRS data sets
508 Eighth quantity of data sPRS data sets
509 Ninth quantity of data sCRS data sets
510 Global sV/Q characteristic values
601 Perfusion phase information
602 Ventilation phase information
620, 621 Special regions of interest (ROI)
631 Heart
632 Left lung
633 Right lung
634 Trachea
635 Aorta
636 Diaphragm
651 ROI_H1, heart
652 ROI_LLcentral, left lung, central
653 ROI_LRcentral, right lung, central
654 ROI_LLdownside, left lung, downside
655 ROI_LRdownside, right lung, downside
656 ROI_H2, aorta
657 ROI_H, heart and aorta
658 ROI_L, entire lung
670 Gradient lines
671 Center of a region of interest
672 Background zone
672 Zones of different intensity
673 Zones of different color
674-677 Various constellations of perfusion and ventilation
901 Visualization means
902 Input means

What is claimed is:

1. A method for processing and visualizing data obtained with a medical device, suitable for generating data for imaging, regarding a perfusion of at least one region of the lung or of at least one region of each of the lung and of the heart, the method comprising the steps of:
   providing a quantity of data based on cardiac- and perfusion-related signals (CPRS) via a signal pattern, of at least one location, within a period of observation;
   determining and providing phase information from the CPRS in relation to at least one comparison variable;
   processing the quantity of data based on CPRS, regarding perfusion of regions of the lung or regions of the lung and of the heart of a patient, taking into account the phase information determined for a determination and providing of a quantity of data, of the at least one location, and a perfusion-specific variable characteristic of the period of observation; and
   generating and providing an output signal for a location-specific visualization of the quantity of data, of the at least one location, and a perfusion-specific variable characteristic of the period of observation.

2. A method in accordance with claim 1, wherein the data obtained with the medical device suitable for imaging comprises data of an electroimpedance tomography (EIT) device.

3. A method in accordance with claim 1, wherein the data obtained with the medical device suitable for imaging are represented as at least one of:
- data of a medical device which provides imaging based on computer tomography (CT);
- data of a medical device which provides imaging based on X-ray;
- data of a medical device which provides imaging based on magnetic resonance tomography (MRT) or nuclear spin tomography; and
- data of a medical device which provides imaging based on sonography (ultrasound).

4. A method in accordance with claim 1, wherein the comparison variable is represented by signals of another location, different from the at least one location, from the quantity of data based on CPRS.

5. A method in accordance with claim 1, wherein the comparison variable is represented by a phase position of the heart from the quantity of data based on CPRS.

6. A method in accordance with claim 1, wherein the comparison variable is represented by signals of at least one location of greatest phase difference from the quantity of data based on CPRS in comparison to the phase positions of the overall quantity of the locations of the quantity of data based on CPRS.

7. A method in accordance with claim 1, further comprising the step of determining a quantity of data based on synchronized cardiac- and perfusion-related signals (sCPRS) from the quantity of data based on CPRS and providing the determined quantity of sCPRS as the at least one characteristic perfusion-specific variable, the sCPRS being determined taking into account the phase information determined, the phase positions of the signals of individual locations relative to each other are matched to each other over time or are synchronized with each other in the period of observation.

8. A method in accordance with claim 1, further comprising the step of providing a quantity of data based on ventilation-related signals (VRS) via a course over time of at least one location regarding ventilation of regions of the lung over a period of observation.

9. A method in accordance with claim 8, further comprising the step of providing a combination of the quantity of data based on CPRS and the quantity of data based on VRS.

10. A method in accordance with claim 9, further comprising distinguishing, in the combination, the quantity of data based on CPRS from the quantity of data based on VRS.

11. A method in accordance with claim 10, further comprising the steps of:
- determining phase information of the VRS in relation to at least one comparison signal; and
- in a step subsequent thereto, determining and providing a quantity of data of at least one location- and ventilation-specific variable characteristic of the period of observation from the quantity of data based on VRS, taking into account the phase information determined.

12. A method in accordance with claim 11, further comprising the step of determining and providing a synchronized quantity of data based on ventilation-related signals (sVRS) from the quantity of data based on VRS, in which the phase positions of the signals of individual locations to each other are matched to each other in the period of observation or are synchronized with each other, taking into account the phase information determined.

13. A method in accordance with claim 8, further comprising the steps of:
- determining and providing a quantity of data based on synchronized ventilation-specific signals (sVRS) from the quantity of data based on VRS, in which the phase positions of the signals of individual locations to each other are matched to each other in the period of observation or are synchronized with each other, taking into account the phase information determined;
- determining a quantity of data based on synchronized cardiac- and perfusion-related signals (sCPRS) from the quantity of data based on CPRS and providing the determined quantity of, the sCPRS being determined taking into account the phase information determined, the phase positions of the signals of individual locations relative to each other are matched to each other over time or are synchronized with each other in the period of observation; and
- matching the quantity of data based on sVRS over time to the quantity of data based on sCPRS and providing a synchronized ventilation-specific quantity of data (sVRS'), synchronized with the perfusion, in the period of observation.

14. A method in accordance with claim 1, further comprising the step of determining special regions of interest in at least one region of the lung on the basis of the phase information determined.

15. A method in accordance with claim 1, further comprising the step of distinguishing the quantity of data based on CPRS from a combination of data of phase information determined and/or defined special regions of interest between a quantity of data based on perfusion-related signals (sPRS) of the lung and a quantity of data based on perfusion-related signals (sCRS) of the heart, and providing the sPRS and sCRS quantities.

16. A method in accordance with claim 15, further comprising the step of determining and providing a variable corresponding to at least one of:
- a pumping capacity of the heart from the quantity of data based on CPRS or on synchronized cardiac- and perfusion-related signals (sCPRS);
- defined special regions of interest;
- a quantity of data based on sPRS of the lung; and
- a quantity of data based on sCRS of the heart.

17. A method in accordance with claim 15, further comprising the steps of:
- providing a quantity of data based on ventilation-related signals (VRS) via a course over time of at least one location regarding ventilation of regions of the lung over a period of observation;
- determining and providing a quantity of data based on synchronized ventilation-specific signals (sVRS) from the quantity of data based on VRS, in which the phase positions of the signals of individual locations to each other are matched to each other in the period of observation or are synchronized with each other, taking into account the phase information determined;
- determining a quantity of data based on synchronized cardiac- and perfusion-related signals (sCPRS) from the quantity of data based on CPRS and providing the determined quantity of, the sCPRS being determined taking into account the phase information determined, the phase positions of the signals of individual locations relative to each other are matched to each other over time or are synchronized with each other in the period of observation;
- matching the quantity of data based on sVRS over time to the quantity of data based on sCPRS and providing a synchronized ventilation-specific quantity of data, synchronized with the perfusion (sVRS'), in the period of observation;

forming a ratio of the quantity of data based on sVRS or the quantity of data based on sVRS to the quantity of data based on sCPRS or to the quantity of data based on sPRS of the lung; and providing the ratio as a synchronized perfusion- and ventilation-specific quantity of data sV/Q over the period of observation as an at least one characteristic location- and perfusion-specific variable.

18. A method in accordance with claim 17, further comprising the step of determining and providing a global sV/Q characteristic value over the period of observation from the sV/Q as the at least one characteristic location- and perfusion-specific variable.

19. A method in accordance with claim 1, wherein a cardiac cycle, a plurality of cardiac cycles, a breathing cycle, a plurality of breathing cycles, parts of cardiac cycles or parts of breathing cycles, parts of a plurality of cardiac cycles or parts of a plurality of breathing cycles are selected as the period of observation.

20. A device for processing and visualizing data obtained by means of a medical device suitable for generating data for imaging regarding a perfusion of at least one region of the lung or of at least one region of each of the lung and of the heart, the device comprising:
a data input unit;
a data output unit;
a calculation and control unit connected to each of the data input unit and the data output unit, the processing and providing a visualization of data obtained by the medical device comprising:
feeding an alternating current or an alternating voltage to at least two electrodes of an electrode array and detecting measured signals at at least two of the electrodes of the electrode array, whereby in a continuous sequence, one after the other another, two electrodes from the plurality of electrodes are selected for feeding the alternating current or alternating voltage, and the measured signals are detected with at least two electrodes from the plurality of electrodes;
generating a quantity of data based on cardiac- and perfusion-related signals (CPRS) by means of a reconstruction algorithm, from the measured signals, and providing the quantity of data based on CPRS;
determining and providing phase information from the CPRS in relation to at least one comparison variable;
processing the quantity of data based on CPRS regarding the perfusion of regions of the lung or regions of the lung and of the heart of a patient, taking into account the phase information determined for a determination and providing of a quantity of data based on at least one location- and cardiac- and perfusion-specific variable characteristic of the period of observation; and
generating and providing an output signal for a display device for a visualization of the quantity of data based on the at least one location- and perfusion-specific variable characteristic of the period of observation to provide a visualization of the quantity of data based on the at least one location- and perfusion-specific variable characteristic of the period of observation on the display device, whereby the at least one location-specific and perfusion-specific variable is visualized numerically, graphically or pictorially over the period of observation.

21. A device in accordance with claim 20, wherein the calculation and control unit generates, on the basis of the phase information, a quantity of data on synchronized cardiac- and perfusion-related signals (sCPRS) as the characteristic location- and perfusion-specific variable and provides same to the data output unit or for a display device.

22. A device in accordance with claim 20, wherein the calculation and control unit generates a quantity of data based on synchronized cardiac- and perfusion-related signals (sCPRS), which sCPRS are synchronized with the phase position of the heart, on the basis of the phase information by means of an equalization of the phase differences and the calculation and control unit provides same to the data output unit for a display device.

23. A device in accordance with claim 20, wherein:
the data input unit is configured for a receipt of a shared quantity of data based on the CPRS and ventilation-specific signals (VRS); and
the calculation and control unit is configured to distinguish the CPRS from the VRS and to provide same as a quantity of data, based on CPRS and as a quantity of data, based on VRS.

24. A device in accordance with claim 20, wherein the calculation and control unit is configured to match to each other or synchronize with each other ventilation-specific signals (VRS) of various regions of the lung in the time reference or in the phase position over a period of observation and to provide same as a quantity of data based on synchronized ventilation-specific signals (sVRS) for the data output unit or to the display device.

25. A device in accordance with claim 20, wherein the calculation and control unit is configured to match ventilation-specific signals (VRS) or synchronized ventilation-specific signals (sVRS) or to synchronize with these in the time reference or in the phase position at the synchronized cardiac- and perfusion-related signals (sCPRS) and to provide same as a quantity of data based on synchronized ventilation-specific signals synchronized with a perfusion (sVRS'), for the data output unit or for a display device.

26. A device in accordance with claim 20, wherein the calculation and control unit determines signals of identical or similar phase position on the basis of the phase information determined and combines or groups the signals of identical or similar phase position into special regions of interest regarding the perfusion of the heart and regarding the perfusion of the lung for at least one region of the lung or of the heart and provides same for the data output unit or for a display device.

27. A device in accordance with claim 20, wherein the calculation and control unit is configured to distinguish a quantity of data based on synchronized cardiac- and perfusion-related signals (sCPRS) or the quantity of data based on CPRS and ventilation-specific signals (VRS) on the basis of the phase information and/or the defined regions of interest from a quantity of data of perfusion-related signals (sPRS) of the lung or a quantity of data of cardiac-related signals (sCRS) of the heart and to provide same for the data output unit or for a display device.

28. A device in accordance with claim 20, wherein the calculation and control unit determines a variable corresponding to the pumping capacity of the heart and provides same for the data output unit or for a display device from the CPRS or synchronized cardiac- and perfusion-related signals (sCPRS) and/or defined special regions of interest (ROI) and/or synchronized perfusion-related signals (sPRS) of the lung and/or the synchronized perfusion-related signals (sCRS) of the heart to determine a pumping performance of the heart or appropriate size and to provide same for the data output unit or the display device.

29. A device or system in accordance with claim 20, wherein the calculation and control unit is configured to combine at least one of the quantities of data based on ventilation-specific signals (VRS, sVRS, sVRS') with at least one of the quantities of data based on synchronized perfusion-related signals (sCPRS, sPRS) into a quantity of data based on location-specific parameters (sV/Q) regarding perfusion and ventilation and to provide same for the data output unit or the display device.

30. A device or system in accordance with claim 29, wherein the calculation and control unit is configured to form a global ventilation-perfusion characteristic value sV/QGlobal as a mean value (sV/QMean), (sV/QMedian) as a minimum value (sV/QMin) or as a maximum value (sV/QMax) from the quantity of data based on location-specific parameters (sV/Q) regarding perfusion and ventilation and to provide same for the data output unit or the display device.

31. A device or system in accordance with claim 30, wherein the data output unit or the display device is configured to output the quantity of data based on location-specific parameters (sV/Q) as a numerical, graphic or pictorial visualization standardized to one of the global ventilation-perfusion characteristic values sV/QMean, sV/QMedian, sV/QMin, sV/QMax.

32. A device for processing and visualizing data obtained by a medical device suitable for generating data for imaging regarding a perfusion of at least one region of the lung or of at least one region of each of the lung and of the heart, the device comprising:
a data input unit for a receipt of data;
a data output unit;
a calculation and control unit connected to each of the data input unit and the data output unit, to provide data as a quantity of data based on cardiac- and perfusion-related signals (CPRS) over a course over time of at least one location over a period of observation, wherein the calculation and control unit:
determines and provides phase information of the CPRS in relation to at least one comparison signal;
processes the quantity of data based on CPRS regarding the perfusion of regions of the lung or regions of the lung and of the heart of a patient, taking into account the phase information;
determines and provides a quantity of data of at least one location- and perfusion-specific variable characteristic of the period of observation;
generates and provides to the data output unit an output signal for a location-specific visualization of the quantity of data of the at least one location- and perfusion-specific variable characteristic of the period of observation.

33. A system for processing and visualizing electroimpedance tomography (EIT) device data regarding a perfusion of at least one region of the lung or of at least one region of each of the lung and of the heart, the system comprising:
an arrangement for processing electroimpedance tomography data, the arrangement comprising a data input unit, a calculation and control unit and a data output unit for the processing of electroimpedance tomography data;
a display device;
an electroimpedance tomography device comprising an electrode array with a plurality of electrodes, an operating electronic unit, a measured value acquisition and analysis unit and a data processing and calculation unit, whereby:
electrodes of the electrode array are arranged on a thorax of a patient;
at least two of the electrodes of the electrode array are configured for a feeding of an alternating current or an alternating voltage;
at least two of the electrodes of the electrode array are configured for a detection of measured signals;
the operating electronic unit is configured for a feeding of the alternating current or the alternating voltage into the electrode,
the measured value acquisition and analysis unit is configured for a detection of the measured signals at the electrodes;
the operating electronic unit and the measured value acquisition and analysis unit are configured to carry out the feeding of the alternating current or of the alternating voltage at at least two of the electrodes and a detection of measured signals at at least two electrodes of the electrode array, such that, in a continuous sequence one after the other, another two electrodes from the electrode array are selected for feeding the alternating current or the alternating voltage, and the measured signals are detected with at least two electrodes of the electrode array;
the data processing and calculation unit is configured to generate a quantity of data based on cardiac- and perfusion-related signals (CPRS) by means of a reconstruction algorithm from the measured signals via a signal pattern of at least one location lying within a period of observation and to provide same to the data input unit for the processing of electroimpedance tomography data;
the calculation and control unit is configured for a determination and providing of phase information of the CPRS in relation to at least one comparison signal;
the calculation and control unit is configured for a processing of the quantity of data based on CPRS regarding the perfusion of regions of the lung or regions of the lung and the heart of a patient, taking into account the phase information determined for a determination and providing of a quantity of data of at least one location- and perfusion-specific variable characteristic of the period of observation;
the data output unit is configured for a generation and providing of an output signal for a location-specific visualization of the quantity of data of the at least one location- and perfusion-specific variable characteristic of the period of observation;
the display device is configured to reproduce a numerical, graphic or pictorial visualization of the at least one location- and perfusion-specific variable characteristic of the period of observation on the basis of the output signal.

34. A method for processing and visualizing data obtained with an electroimpedance tomography (EIT) device regarding a perfusion of at least one lung region or of at least each of one lung region and of the heart via a signal pattern of at least one location lying within a period of observation by means of an electrode array containing a plurality of electrodes arranged at or about the thorax of a patient, the method comprising the steps of:
feeding an alternating current or an alternating voltage to at least two of the electrodes of the electrode array and detecting measured signals at at least two of the electrodes of the electrode array, whereby in a continuous sequence, one after the other another, two electrodes from the plurality of electrodes are selected for feeding the alternating current or alternating voltage, and the measured signals are detected with at least two electrodes from the plurality of electrodes;
generating and providing a quantity of data based on cardiac- and perfusion-related signals (CPRS) by means of a reconstruction algorithm from the measured signals and providing the quantity of data based on CPRS;

determining and providing phase information from the CPRS in relation to at least one comparison variable;

processing the quantity of data based on CPRS regarding the perfusion of regions of the lung or regions of the lung and of the heart of a patient, taking into account the phase information determined for a determination and providing of a quantity of data based on at least one location- and cardiac- and perfusion-specific variable characteristic of the period of observation;

generating and providing an output signal to a display device for a visualization of the quantity of data based on the at least one location- and perfusion-specific variable characteristic of the period of observation;

providing a visualization of the quantity of data based on the at least one location- and perfusion-specific variable characteristic of the period of observation on the display device, whereby the at least one location-specific and perfusion-specific variable is visualized numerically, graphically or pictorially over the period of observation.

* * * * *